United States Patent [19]
Rasmussen et al.

[11] Patent Number: 5,948,672
[45] Date of Patent: Sep. 7, 1999

[54] CELLULASE PREPARATION COMPRISING AN ENDOGLUCANASE ENZYME

[75] Inventors: Grethe Rasmussen, Copenhagen; Jan Møller Mikkelsen, Gentofte; Martin Schülein, Copenhagen; Shamkant Anant Patkar, Lyngby, all of Denmark; Fred Hagen, Seattle, Wash.; Carsten Mailand Hjort, Roskilde; Sven Hastrup, Copenhagen, both of Denmark

[73] Assignee: Novo Nordisk A/S, Bagsvaerd, Denmark

[21] Appl. No.: 08/389,423

[22] Filed: Feb. 14, 1995

Related U.S. Application Data

[63] Continuation of application No. 07/946,489, filed as application No. PCT/DK91/00123, May 8, 1991, abandoned.

[30] Foreign Application Priority Data

May 9, 1990 [DK] Denmark ................................ 1159/90
Apr. 22, 1991 [DK] Denmark .................................. 736/91

[51] Int. Cl.$^6$ ........................... D06M 16/00; C12N 9/24; D21C 1/00; D21C 3/00
[52] U.S. Cl. .......................... 435/264; 435/200; 435/263; 435/277; 435/278
[58] Field of Search .................................... 435/200, 263, 435/264, 277, 278; 252/177.12

[56] References Cited

U.S. PATENT DOCUMENTS 4,435,307  3/1984  Barbesgaard et al. ............. 252/174.12

FOREIGN PATENT DOCUMENTS

WO 89/09259  10/1989  WIPO .

OTHER PUBLICATIONS

Hames et al., Gel Electrophoresis of Proteins (1981) 14–19.
Hayashida et al., Methods in Enzymology (1988) 160:323–332.
Hayashida et al., Agric. Biol. Chem. (1980) 44(8):1721–1728.
Kraulis et al., Biochemistry (1989) 28:7241–7257.
Pentilla et al., Yeast (1987) 3:175–185.
Pentilla et al., Gene (1986) 45:253–263.
Saloheimo et al., Gene (1988) 63:11–21.
Schülein et al., Foundation for Biotechnical and Industrial Fermentation Research (1993) 8:109–116.
Wood et al., Methods in Enzymology, vol. 160, pp. 323–332 (1988).
Poulsen et al., Chem. Abs., vol. 107, No. 9, p. 292, No. 73161r (1987).
Klesov et al., Chem. Abs., vol. 106, No. 17, p. 302, No. 134159z (1987).
Ortega, Chem. Abs., vol. 114, No. 15, p. 619, No. 141530g (1991).
Hayashida et al., Chem. Abs., vol. 105, No. 3, p. 316, No. 20820g (1986).
Rao et al, Chem. Abs., vol. 105, No. 13, p. 307, No. 110894p (1986).
Janson, TIBS vol. 2, No. 2 pp. 31–38 (1984).
Ortega Chem Abs., vol. 114, No. 15 p. 619 No. 141330g (1991).

*Primary Examiner*—Lisa Hobbs
*Attorney, Agent, or Firm*—Steve T. Zelson, Esq.; Reza Green, Esq.

[57] ABSTRACT

A cellulase preparation consisting essentially of a homogeneous endoglucanase component which is immunoreactive with an antibody raised against a highly purified ~43 kD endoglucanase derived from *Humicola insolens*, DSM 1800, or which is homogeneous to said ~43 kD endoglucanase, may be employed in the treatment cellulose-containing fabrics for harshness reduction or color clarification or to provide a localized variation in the color of such fabrics, or it may be employed in the treatment of paper pulp.

20 Claims, 2 Drawing Sheets

CELLULASE PREPARATION COMPRISING AN ENDOGLUCANASE ENZYME

This application is a continuation of application Ser. No. 07/946,489, filed Nov. 25, 1992, now abandoned, which is the National Stage application of PCT/DK91/00123, filed May 8, 1991, abandoned, the contents of which are incorporated herein by reference.

FIELD OF INVENTION

The present invention concerns a cellulase preparation comprising a single-component endoglucanase, a detergent additive comprising the cellulase preparation, a detergent composition containing the cellulase preparation as well as methods of treating cellulose-containing fabrics with the cellulase preparation.

BACKGROUND OF THE INVENTION

It is well known in the art that repeated washing of cotton-containing fabrics generally causes a pronounced, unpleasant harshness in the fabric, and several methods for overcoming this problem have previously been suggested in the art. For example GB 1,368,599 of Unilever Ltd. teaches the use of cellulytic enzymes for reducing the harshness of cotton-containing fabrics. Also, U.S. Pat. No. 4,435,307 (of Novo Industri A/S) teaches the use of a cellulytic enzyme derived from *Humicola insolens* as well as a fraction thereof, designated $AC_xI$, as a harshness reducing detergent additive. Other uses of cellulytic enzymes mentioned in the art involve soil removal from and colour clarification of fabric (cf. for instance EP 220 016), providing increasing water absorption (JP-B-52-48236) and providing a localized variation in colour to give the treated fabrics a "stone-washed" appearance (EP 307,564). Cellulytic enzymes may furthermore be used in the brewing industry for the degradation of β-glucans, in the baking industry for improving the properties of flour, in paper pulp processing for removing the non-crystalline parts of cellulose, thus increasing the proportion of crystalline cellulose in the pulp, and for improving the drainage properties of pulp, and in animal feed for improving the digestibility of glucans.

The practical exploitation of cellulytic enzymes has, to some extent, been set back by the nature of the known cellulase preparations which are often complex mixtures. It is difficult to optimise the production of multiple enzyme systems and thus to implement industrial cost-effective production of cellulytic enzymes, and their actual use has been hampered by difficulties arising from the need to apply rather large quantities of the cellulytic enzymes to achieve the desired effect on cellulosic fabrics.

The drawbacks of previously suggested cellulase preparations may be remedied by using preparations comprising a higher amount of endoglucanases. A cellulase preparation enriched in endoglucanase activity is disclosed in WO 89/00069.

SUMMARY OF THE INVENTION

A single endoglucanase component has now been isolated which exhibits favourable activity levels relative to cellulose-containing materials.

Accordingly, the present invention relates to a cellulase preparation consisting essentially of a homogeneous endoglucanase component which is immunoreactive with an antibody raised against a highly purified ~43 kD endoglucanase derived from *Humicola insolens,* DSM 1800, or which is homologous to said ~43 kD endoglucanase.

The finding that this particular endoglucanase component of cellulase is advantageous for the treatment of cellulose-containing materials is of considerable practical significance: it permits a cost-effective production of the cellulase, e.g. by employing recombinant DNA techniques for producing the active component, and makes the actual effective application of the enzyme feasible in that a smaller quantity of the cellulase preparation is requested to produce the desired effect on cellulosic materials.

DETAILED DISCLOSURE OF THE INVENTION

Figure 1:
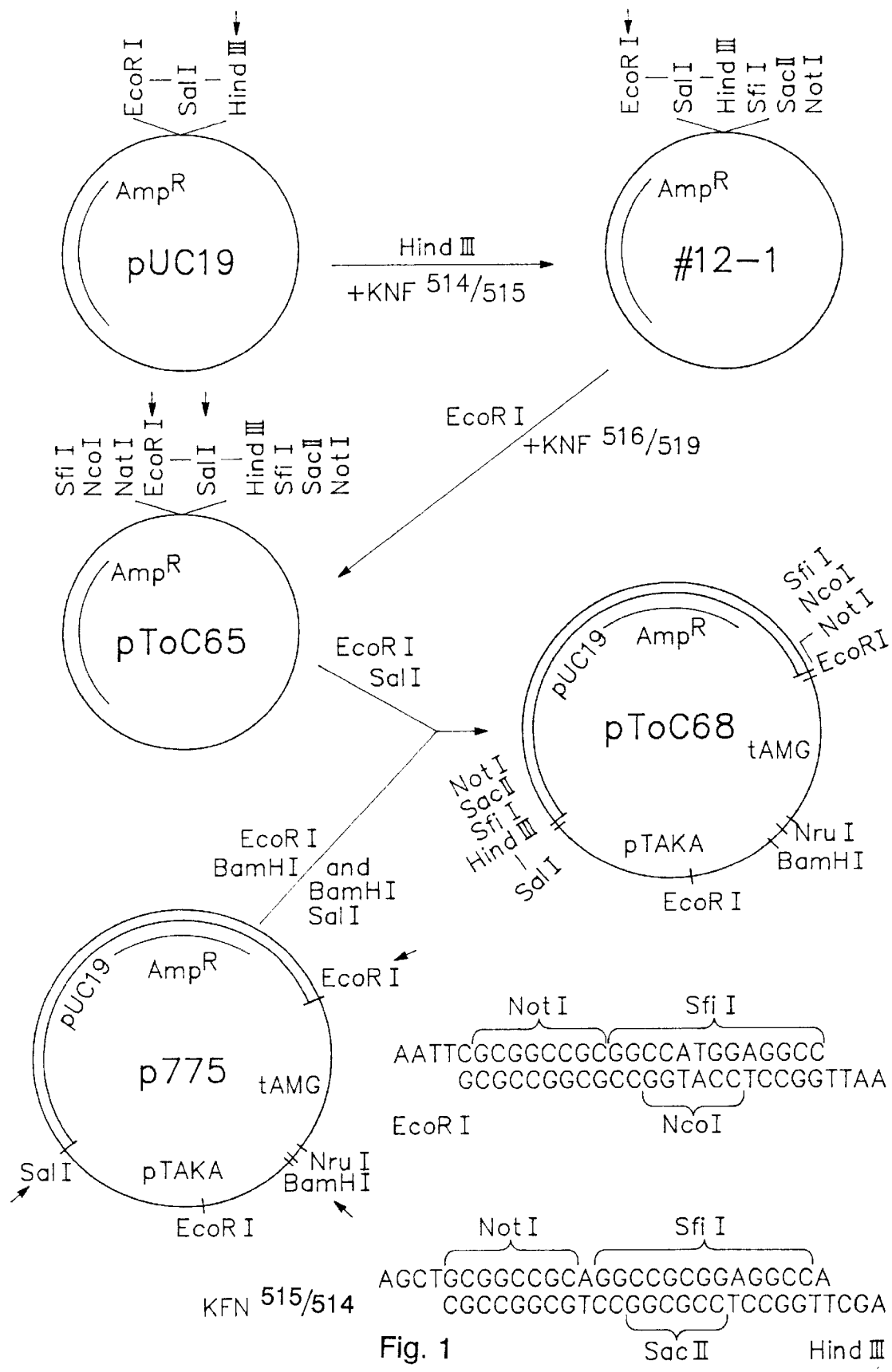
FIG. 1 illustrates the creation of the Aspergillus expression vector pToC 68.

The cellulase preparation of the invention is advantageously one in which the endoglucanase component exhibits a CMC-endoase activity of at least about 50 CMC-endoase units per mg of total protein.

In the present context, the term "CMC-endoase activity" refers to the endoglucanase activity of the endoglucanase component in terms of its ability to degrade cellulose to glucose, cellobiose and triose, as determined by a viscosity decrease of a solution of carboxymethyl cellulose (CMC) after incubation with the cellulase preparation of the invention, as described in detail below.

Preferred cellulase preparations of the invention are those in which the endoglucanase component exhibits a CMC-endoase activity of at least about 60, in particular at least about 90, CMC-endoase units per mg of total protein. In particular, a preferred endoglucanase component exhibits a CMC-endoase activity of at least 100 CMC-endoase units per mg of total protein.

The CMC-endoase (endoglucanase) activity can be determined from the viscosity decrease of CMC, as follows:

A substrate solution is prepared, containing 35 g/l CMC (Hercules 7 LFD) in 0.1 M tris buffer at pH 9.0. The enzyme sample to be analyzed is dissolved in the same buffer.

10 ml substrate solution and 0.5 ml enzyme solution are mixed and transferred to a viscosimeter (e.g. Haake VT 181, NV sensor, 181 rpm), thermostated at 40° C.

Viscosity readings are taken as soon as possible after mixing and again 30 minutes later. The amount of enzyme that reduces the viscosity to one half under these conditions is defined as 1 unit of CMC-endoase activity.

SDS polyacrylamide gel electrophoresis (SDS-PAGE) and isoelectric focusing with marker proteins in a manner known to persons skilled in the art were used to determine the molecular weight and isoelectric point (pI), respectively, of the endoglucanase component in the cellulase preparation of the invention. In this way, the molecular weight of a specific endoglucanase component was determined to be ≈43 kD. The isoelectric point of this endoglucanase was determined to be about 5.1. The immunochemical characterization of the endoglucanase was carried out substantially as described in WO 89/00069, establishing that the endoglucanase is immunoreactive with an antibody raised against highly purified ~43 kD endoglucanase from *Humicola insolens,* DSM 1800. The cellobiohydrolase activity may be defined as the activity towards cellobiose p-nitrophenyl. The activity is determined as μmole nitrophenyl released per minute at 37° C. and pH 7.0. The present endoglucanase component was found to have essentially no cellobiohydrolase activity.

The endoglucanase component in the cellulase preparation of the invention has initially been isolated by extensive purification procedures, i.a. involving reverse phase HPLC purification of a crude *H. insolens* cellulase mixture according to U.S. Pat. No. 4,435,307 (cf. Example 1 below). This procedure has surprisingly resulted in the isolation of a ~43 kD endoglucanase as a single component with unexpectedly favourable properties due to a surprisingly high endoglucanase activity.

In another aspect, the present invention relates to an enzyme exhibiting endoglucanase activity (in the following referred to as an "endoglucanase enzyme"), which enzyme has the amino acid sequence SEQ ID NO:2, or a homologue thereof exhibiting endoglucanase activity. In the present context, the term "homologue" is intended to indicate a polypeptide encoded by DNA which hybridizes to the same probe as the DNA coding for the endoglucanase enzyme with this amino acid sequence under certain specified conditions (such as presoaking in 5×SSC and prehybridizing for 1 h at ~40° C. in a solution of 20% formamide, 5×Denhardt's solution, 50 mM sodium phosphate, pH 6.8, and 50 μg of denatured sonicated calf thymus DNA, followed by hybridization in the same solution supplemented with 100 μM ATP for 18 h at ~40° C.). The term is intended to include derivatives of the aforementioned sequence obtained by addition of one or more amino acid residues to either or both the C- and N-terminal of the native sequence, substitution of one or more amino acid residues at one or more sites in the native sequence, deletion of one or more amino acid residues at either or both ends of the native amino acid sequence or at one or more sites within the native sequence, or insertion of one or more amino acid residues at one or more sites in the native sequence.

The endoglucanase enzyme of the invention may be one producible by species of Humicola such as *Humicola insolens* e.g strain DSM 1800, deposited on Oct. 1, 1981 at the Deutsche Sammlung von Mikroorganismen, Mascheroder Weg 1B, D-3300 Braunschweig, FRG, in accordance with the provisions of the Budapest Treaty on the International Recognition of the Deposit of Microorganisms for the Purposes of Patent Procedure (the Budapest Treaty).

In a further aspect, the present invention relates to an endoglucanase enzyme which has the amino acid sequence SEQ ID NO:4, or a homologue thereof (as defined above) exhibiting endoglucanase activity. Said endoglucanase enzyme may be one producible by a species of Fusarium, such as *Fusarium oxysporum,* e.g. strain DSM 2672, deposited on Jun. 6, 1983 at the Deutsche Sammlung von Mikroorganismen, Mascheroder Weg 1B, D-3300 Braunschweig, FRG, in accordance with the provisions of the Budapest Treaty.

Furthermore, it is contemplated that homologous endoglucanases may be derived from other microorganisms producing cellulolytic enzymes, e.g. species of Trichoderma, Myceliophthora, Phanerochaete, Schizophyllum, Penicillium, Aspergillus, and Geotricum.

The present invention also relates to a DNA construct comprising a DNA sequence encoding an endoglucanase enzyme as described above, or a precursor form of the enzyme. In particular, the DNA construct has a DNA sequence as SEQ ID NO:1 or SEQ ID NO:3, or a modification thereof. Examples of suitable modifications of the DNA sequence are nucleotide substitutions which do not give rise to another amino acid sequence of the endoglucanase, but which correspond to the codon usage of the host organism into which the DNA construct is introduced or nucleotide substitutions which do give rise to a different amino acid sequence and therefore, possibly, a different protein structure which might give rise to an endoglucanase mutant with different properties than the native enzyme. Other examples of possible modifications are insertion of one or more nucleotides into the sequence, addition of one or more nucleotides at either end of the sequence, or deletion of one or more nucleotides at either end or within the sequence.

The DNA construct of the invention encoding the endoglucanase enzyme may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *EMBO Journal* 3, 1984, pp. 801–805. According to the phosphoamidite method, oligonucleotides are synthesized, e.g. in an automatic DNA synthesizer, purified, annealed, ligated and cloned in suitable vectors.

A DNA construct encoding the endoglucanase enzyme or a precursor thereof may, for instance, be isolated by establishing a cDNA or genomic library of a cellulase-producing microorganism, such as *Humicola insolens,* DSM 1800, and screening for positive clones by conventional procedures such as by hybridization using oligonucleotide probes synthesized on the basis of the full or partial amino acid sequence of the endoglucanase in accordance with standard techniques (cf. Sambrook et al., *Molecular Cloning: A Laboratory Manual,* 2nd. Ed., Cold Spring Harbor, 1989), or by selecting for clones expressing the appropriate enzyme activity (i.e. CMC-endoase activity as defined above), or by selecting for clones producing a protein which is reactive with an antibody against a native cellulase (endoglucanase).

Finally, the DNA construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire DNA construct, in accordance with standard techniques. The DNA construct may also be prepared by polymerase chain reaction using specific primers, for instance as described in U.S. Pat. No. 4,683,202 or R. K. Saiki et al., *Science* 239, 1988, pp. 487–491.

The invention further relates to a recombinant expression vector into which the DNA construct of the invention is inserted. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the endoglucanase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the endoglucanase, the promoter and the terminator, respectively, and to insert them into suitable vectors are well known to persons skilled in the art (cf., for instance, Sambrook et al., op.cit.).

The invention also relates to a host cell which is transformed with the DNA construct or the expression vector of the invention. The host cell may for instance belong to a species of Aspergillus, most preferably *Aspergillus oryzae* or *Aspergillus niger*. Fungal cells may be transformed by a process involving protoplast formation and transformation of the protoplasts followed by regeneration of the cell wall in a manner known per se. The use of Aspergillus as a host microorganism is described in EP 238,023 (of Novo Industri A/S), the contents of which are hereby incorporated by reference. The host cell may also be a yeast cell, e.g. a strain of *Saccharomyces cerevisiae*.

Alternatively, the host organism may be a bacterium, in particular strains of Streptomyces and Bacillus, and *E. coli*. The transformation of bacterial cells may be performed according to conventional methods, e.g. as described in Sambrook et al., *Molecular Cloning: A Laboratory Manual*, Cold Spring Harbor, 1989.

The present invention further relates to a process for producing an endoglucanase enzyme of the invention, the process comprising culturing a host cell as described above in a suitable culture medium under conditions permitting the expression of the endoglucanase enzyme, and recovering the endoglucanase enzyme from the culture. The medium used to culture the transformed host cells may be any conventional medium suitable for growing the host cells in question. The expressed endoglucanase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

By employing recombinant DNA techniques as indicated above, techniques of protein purification, techniques of fermentation and mutation or other techniques which are well known in the art, it is possible to provide endoglucanases of a high purity.

The cellulase preparation or endoglucanase enzyme of the invention may conveniently be added to cellulose-containing fabrics together with other detergent materials during soaking, washing or rinsing operations. Accordingly, in another aspect, the invention relates to a detergent additive comprising the cellulase preparation or endoglucanase enzyme of the invention. The detergent additive may suitably be in the form of a non-dusting granulate, stabilized liquid or protected enzyme. Non-dusting granulates may be produced e.g. according to U.S. Pat. Nos. 4,106,991 and 4,661,452 (both to Novo Industri A/S) and may optionally be coated by methods known in the art. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent additive may suitably contain 1–500, preferably 5–250, most preferably 10–100 mg of enzyme protein per gram of the additive. It will be understood that the detergent additive may further include one or more other enzymes, such as a protease, lipase, peroxidase or amylase, conventionally included in detergent additives.

According to the invention, it has been found that when the protease is one which has a higher degree of specificity than *Bacillus lentus* serine protease, an increased storage stability of the endoglucanase enzyme is obtained. (For the present purpose, a protease with a higher degree of specificity than *B. lentus* serine protease is one which degrades human insulin to fewer components than does the *B. lentus* serine protease under the following conditions: 0.5 ml of a 1 mg/ml solution of human insulin in B and R buffer, pH 9.5, is incubated with 75 $\mu$l enzyme solution of 0.6 CPU [cf. Novo Nordisk Analysis Methods No. AF 228/1] per liter for 120 min. at 37° C., and the reaction is quenched with 50 $\mu$l 1N HCl). Examples of such proteases are subtilisin Novo or a variant thereof (e.g. a variant described in U.S. Pat. No. 4,914,031), a protease derivable from *Nocardia dassonvillei* NRRL 18133 (described in WO 88/03947), a serine protease specific for glutamic and aspartic acid, producible by *Bacillus licheniformis* (this protease is described in detail in co-pending International patent application No. PCT/DK91/00067), or a trypsin-like protease producible by Fusarium sp. DSM 2672 (this protease is described in detail in WO 89/06270).

In a still further aspect, the invention relates to a detergent composition comprising the cellulase preparation or endoglucanase enzyme of the invention.

Detergent compositions of the invention additionally comprise surfactants which may be of the anionic, non-ionic, cationic, amphoteric, or zwitterionic type as well as mixtures of these surfactant classes. Typical examples of anionic surfactants are linear alkyl benzene sulfonates (LAS), alpha olefin sulfonates (AOS), alcohol ethoxy sulfates (AES) and alkali metal salts of natural fatty acids. It has, however, been observed that the endoglucanase is less stable in the presence of anionic detergents and that, on the other hand, it is more stable in the presence of non-ionic detergents or certain polymeric compounds such as polyvinylpyrrolidone, polyethylene glycol or polyvinyl alcohol. Consequently, the detergent composition may contain a low concentration of anionic detergent and/or a certain amount of non-ionic detergent or stabilising polymer as indicated above.

Detergent compositions of the invention may contain other detergent ingredients known in the art as e.g. builders, bleaching agents, bleach activators, anti-corrosion agents, sequestering agents, anti soil-redeposition agents, perfumes, enzyme stabilizers, etc.

The detergent composition of the invention may be formulated in any convenient form, e.g. as a powder or liquid. The enzyme may be stabilized in a liquid detergent by inclusion of enzyme stabilizers as indicated above. Usually, the pH of a solution of the detergent composition of the invention will be 7–12 and in some instances 7.0–10.5. Other detergent enzymes such as proteases, lipases or amylases may be included the detergent compositions of the invention, either separately or in a combined additive as described above.

The softening, soil removal and colour clarification effects obtainable by means of the cellulase preparation of the invention generally require a concentration of the cellulase preparation in the washing solution of 0.0001–100, preferably 0.0005–60, and most preferably 0.01–20 mg of enzyme protein per liter. The detergent composition of the invention is typically employed in concentrations of 0.5–20 g/l in the washing solution. In general, it is most convenient to add the detergent additive in amounts of 0.1–5% w/w or, preferably, in amounts of 0.2–2% of the detergent composition.

In a still further aspect, the present invention relates to a method of reducing the rate at which cellulose-containing fabrics become harsh or of reducing the harshness of cellulose-containing fabrics, the method comprising treating cellulose-containing fabrics with a cellulase preparation or endoglucanase enzyme as described above. The present invention further relates to a method providing colour clarification of coloured cellulose-containing fabrics, the method comprising treating coloured cellulose-containing fabrics with a cellulase preparation or endoglucanase, and a method of providing a localized variation in colour of coloured cellulose-containing fabrics, the method comprising treating coloured cellulose-containing fabrics with a cellulase preparation or endoglucanase of the invention. The methods of the invention may be carried out by treating cellulose-containing fabrics during washing. However, if desired, treatment of the fabrics may also be carried out during soaking or rinsing or simply by adding the cellulase preparation or the endoglucanase enzyme to water in which the fabrics are or will be immersed.

According to the invention, it has been found that the drainage properties of paper pulp may be significantly improved by treatment with the endoglucanase of the invention without any significant concurrent loss of strength. Consequently, the present invention further relates to a method of improving the drainage properties of pulp, the method comprising treating paper pulp with a cellulase preparation or an endoglucanase enzyme according to the invention. Examples of pulps which may be treated by this method are waste paper pulp, recycled cardboard pulp, kraft pulp, sulphite pulp, or thermomechanical pulp and other high-yield pulps.

The present invention is described in further detail with reference to currently preferred embodiments in the following examples which are not intended to limit the scope of the invention in any way.

EXAMPLES

Example 1

Isolation of a ~43 kD Endoglucanase from
Humicola insolens

1. Preparation of a rabbit antibody reactive with a ~43 kD endoglucanase purified from *Humicola insolens* cellulase mixture Cellulase was produced by cultivating *Humicola insolens* DSM 1800, as described in U.S. Pat. No. 4,435,307, Example 6. The crude cellulase was recovered from the culture broth by filtration on diatomaceous earth, ultrafiltration and freeze-drying of the retentate, cf. Examples 1 and 6 of U.S. Pat. No. 4,435,307.

The crude cellulase was purified as described in WO 89/09259, resulting in the fraction F1P1C2 which was used for the immunization of mice. The immunization was carried out 5 times at bi-weekly intervals, each time using 25 pg protein including Freund's Adjuvant.

Hybridoma cell lines were established as described in Ed Harlow and David Lane, *Antibodies. A Laboratory Manual*, Cold Spring Harbor Laboratory 1988. The procedure may briefly be described as follows:

After bleeding the mouse and showing that the mouse serum reacts with proteins present in the F1P1C2 fraction, the spleen was removed and homogenized and then mixed with PEG and Fox-river myeloma cells from Hyclone, Utah, USA.

The hybridomas were selected according to the established HAT screening procedure.

The recloned hybridoma cell lines were stabilized. The antibodies produced by these cell lines were screened and selected for belonging to the IgG1 subclass using a commercial mouse monoclonal typing kit from Serotec, Oxford, England. Positive antibodies were then screened for reactivity with F1P1C2 in a conventional ELISA, resulting in the selection of F4, F15 and F41 as they were all very good in ELISA response but were found to have different response in immunoblotting using crude *H. insolens,* DSM 1800, cellulase in SDS-PAGE followed by Western Blot, indicating that they recognized different epitopes.

The three antibodies were produced in large quantities in the ascites fluid of $CRBF_1$ mice. The mouse gammaglobulin was purified from ascites fluid by protein A purification using protein A coupled to Sepharose (Kem.En.Tek., Copenhagen, Denmark).

The different monoclonal gammaglobulins were tested for response in a sandwich ELISA using each monoclonal antibody as the catching antibody, various HPLC fractions of Celluzyme as the antigen, and a rabbit antibody raised against endoglucanase B from Celluzyme as the detection antibody.

To visualize binding in the ELISA, a porcine antibody against rabbit IgG covalently coupled to peroxidase from Dakopatts (Copenhagen, Denmark) and was visualized with OPD(1,2-phenylenediamine, dihydrochoride)/$H_2O_2$.

The highest ELISA response was obtained with the monoclonal antibody F41 which was therefore used in the immunoaffinity purification steps.

The purified mouse gammaglobulin F41 was coupled to 43 g of CNBr-activated Sepharose 4B as described by the manufacturer (Pharmacia, Sweden) followed by washing.

2. Immunoaffinity purification of ~43 kD endoglucanase from a *H. insolens* cellulase mixture

*H. insolens* cellulase mixture (as described above) was diluted to 3% dry matter, and the pH was adjusted to 3.5 in 15 min. at 4° C. The precipitate was removed by filtration after adjusting the pH to 7.5. Then sodium sulphate was added to precipitate the active enzyme and this was done at 40° C. (260 gram per kg at pH 5.5). The precipitate was solubilized with water and filtered. The acid treatment was repeated. Finally, the product was filtered and concentrated by ultrafiltration sing a polyvinylsulphonate membrane with a 10,000 Mw cut-off.

The cellulase product was then diluted to 3% dry matter, adjusting the pH to 9.0, and subjected to anion exchange chromatography on a DEAE-Sepharose column as recommended by the manufacturer (Pharmacia, Sweden).

The protease-free cellulase product was applied on the F 41 gammaglobulin-coupled Sepharose column described above at pH 8.0 in sodium phoshate buffer.

After application the column was washed with the same buffer containing 0.5 M sodium chloride. The column was then washed with 0.1 M sodium acetate buffer containing 0.5 M sodium chloride, pH 4.5, after which the column was washed in 5 mM sodium acetate buffer, pH 4.5. Finally, the ~43 kD endoglucanase was eluted with 0.1 M citric acid.

Total yield: 25 mg with an endoglucanase activity of 1563 CMC-endoase units.

The eluted protein migrates as a single band in SDS-PAGE with an apparent MW of ~43 kD and a pI after isoelectric focusing of about 5.0 to 5.2.

Inactive protein was removed by reverse phase purification.

Inactive and active protein was separated by HPLC using a gradient of 2-propanol. Inactive protein elutes at about 25% 2-propanol and the active ~43 kD endoglucanase elutes at 30% 2-propanol, the active endoglucanase being detectable by a CMC-Congo Red clearing zone.

In this way, a total of 0.78 mg active protein was recovered with 122 CMC endoase units. This procedure was repeated 30 times.

The ~43 kD endoglucanase was recovered by first freeze-drying to remove the TFA and propanol and then solubilizing in phosphate buffer.

The endoglucanase activity of the purified material was 156 CMC-endoase units per mg protein and the total yield including freze-drying was 65% of the endoglucanase activity.

The thus obtained ~43 kD enzyme was used to immunise rabbits according to the procedure described by N. Axelsen et al. in *A Manual of Quantitative Immunolelectrophoresis*, Blackwell Scientific Publications, 1973, Chapter 23. Purified immunoglobulins were recovered from the antisera by ammonium sulphate precipitation followed by dialysis and ion exchange chromatography on DEAE-Sephadex in a manner known per se. Binding of purified immunoglobulin to the endoglucanase was determined, and the rabbit immunoglobulin AS 169 was selected for further studies.

2. Characterization of the ~43 kD endoglucanase

Amino acid composition: Using total hydrolysis, the following composition was obtained after amino acid analysis:

| | |
|---|---|
| Asp | 17 |
| Asn | 15 |
| Thr | 25 |
| Ser | 29 |
| Glu | 6 |
| Gln | 13 |
| Pro | 21 |
| Gly | 32 |
| Ala | 23 |
| Cys | 20 |
| Val | 14 |
| Met | 1 |
| Ile | 7 |
| Leu | 8 |
| Tyr | 6 |
| Phe | 15 |
| Lys | 9 |
| His | 2 |
| Trp | 9 |
| Arg | 12 |

The Mw of the non-glycosylated protein was estimated to be 30,069 based on the amino acid composition. The glycosylation was measured to

| | |
|---|---|
| Galactose | 10 |
| Mannose | 28 | corresponding to a Mw of 6,840, resulting in a total Mw of the endoglucanase of 36,900 (±2,400). The extinction coefficient per mole was estimated as follows:

| | |
|---|---|
| Tryptophan | 9 times 5690 |
| Tyrosine | 6 times 1280 |
| Cysteins | 20 times 120 |
| total | 61290 per mole. |

Extinction coefficients are 1.66 at 280 nm corresponding to 1 mg protein per ml. (Reference: S. C. Gill and P. Hippel, *Anal. Biochemistry* 182, 312–326 (1989).)

The amino acid sequence was determined on an Applied Biosystems 475A Protein Sequenator using Edman degradation. Only one sequence indicated the purity of the protein. The amino acid sequence is SEQ ID NO:2.

Enzyme Properties

The enzyme is stable between pH 3 and 9.5.

The enzyme does not degrade highly crystalline cellulose or the substrate cellobiose $\beta$-p-nitrophenyl, (Cellobiohydrolase substrate), but degrades amorphous cellulose mainly to cellobiose, cellotriose and cellotetraose, indicating that the enzyme may be used to produce cellodextrins from insoluble amorphous cellulose.

The enzyme is active between pH 6.0 and 10.0 with a maximum activity at about 50° C.

Example 2

Cloning and Expression of the ~43 kD Endoglucanase in *Aspergillus oryzae*

Partial cDNA

A cDNA library was made from *Humicola insolens* strain DSM 1800 mRNA (Kaplan et al. (1979) Biochem.J. 183, 181–184) according to the method of Okayama and Berg (1982) Mol. Cell. Biol. 2, 161–170. This library was screened by hybridization with radioactively labelled oligonucleotides to filters with immobilized DNA from the recombinants (Gergen et al. (1979) Nucleic Acids Res. 7, 2115–2136). The oligonucleotide probes were made on the basis of amino acid sequences of tryptic fragments of the purified ~43 kD endoglucanase. A colony was found to hybridize to three different probes (NOR 1251, 2048, and 2050) and was isolated. The sequence showed that the inserted 680 bp cDNA coded for the C-terminal 181 amino acids of the ~43 kD protein and the 3' nontranslated mRNA. A 237 bp long Pvu I -Xho I fragment from this clone was used to probe a Northern blot (as described in Sambrook et al, op. cit., p. 7.40–7.42 and p. 7.46–7.48.) with *H. insolens* mRNA and it was shown that the entire ~43 kD mRNA has a length of app. 1100 bp. The same 237 bp fragment was used to probe a genomic library from the same strain.

Genomic Clone

A *Humicola insolens* strain DSM 1800 genomic library was made from total DNA prepared by the method of Yelton (M. M. Yelton et al. (1984) Proc. Natl. Acad. Sci. USA. 81. 1470–1474) and partially digested with Sau 3A. Fragments larger than 4 kb were isolated from an agarose gel and ligated to pBR 322 digested with Bam H1 and dephosphorylated. The ligation products was transformed into *E. coli* MC1000 (Casadaban and Cohen (1980). J. Mol. Biol., 138, 179–207) made r⁻m⁺ by conventional methods. 40,000 recombinants were screened with the 237 bp Pvu I -Xho I partial cDNA fragment described in the paragraph "partial CDNA". 2 colonies that contained the entire ~43 kD endoglucanase sequence were selected and the gene was sequenced by the dideoxy method using the Sequenase® kit (United States Biochemical Corporation) according to the manufacturer's instructions. The sequence was identical to the sequence of the full length cDNA gene (see the paragraph "full length CDNA" below) except for one intron in the genomic gene.

The genomic gene was amplified by the PCR method using a Perkin-Elmer/Cetus DNA Amplification System according to the manufacturer's instructions. In the 5' end of the gene the primer NOR 2378 was used. This primer is a 25 mer matching the 5' untranslated end of the gene except for one C to T replacement generating a Bcl I site. In the 3' end of the gene the primer NOR 2389 was used. This primer is a 26 mer of which 21 bases match the 3' untranslated part of the gene and the 5 bases in the 5' end of the primer completes a Sal I site.

The Aspergillus expression vector pToC 68 was constructed from plasmid p775 (the construction of which is described in EP 238 023) by insertion of the following linkers

```
KFN 514:  5'-AGCTGCGGCCGCAGGCCGCGGAGGCCA-3'       (SEQ ID NO:5)

KFN 515:      3'-CGCCGGCGTCCGGCGCCTCCGGTTCGA-5'   (SEQ ID NO:6)
                           SacII      HindIII EcoRI NotI     StiI
KFN 516:  5'-AATTCGCGGCCGCGGCCATGGAGGCC-3'        (SEQ ID NO:7)

KFN 519:      3'-GCGCCGGCGCCGGTACCTCCGGTTAA-5'    (SEQ ID NO:8)
                            NcoI
```

The construction of pToC is shown in the appended FIG. 1.

The PCR fragment obtained above was digested with Bcl I and Sal I and inserted into pToC 68 digested with Bam HI and Xho I. The insert of the resulting plasmid (pCaHj 109) was sequenced and shown to be identical to the original clone.

Full Length cDNA

Figure 2:
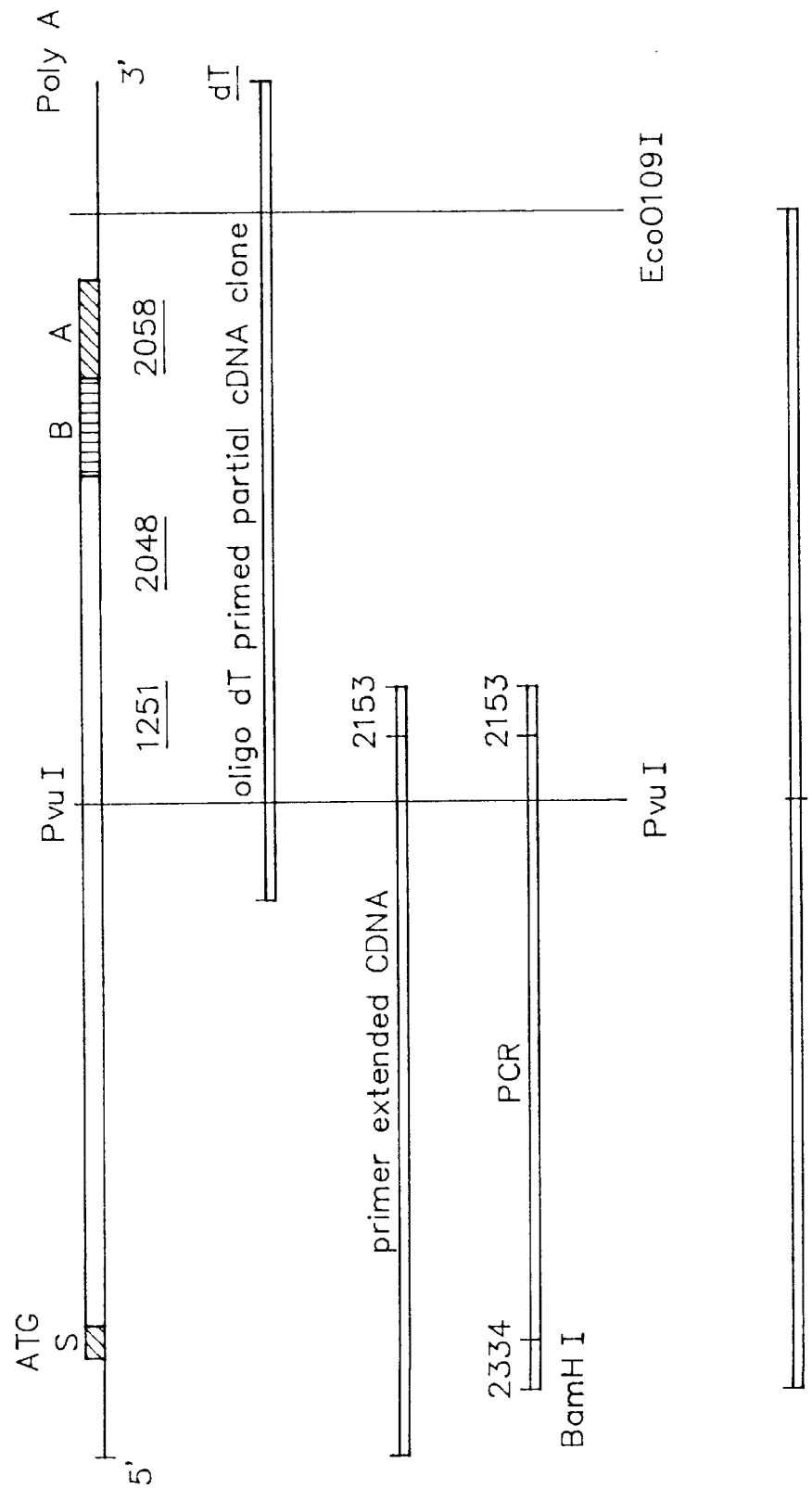
FIG. 2 illustrates the cloning strategy for the cloning of the full-length cDNA molecule encoding the 43 kD endoglucanase from *Humicola insolens* strain DSM 1800.

First strand cDNA was synthesized from a specific primer within the known sequence (NOR 2153), and second strand synthesis was made by the method described by Gubler and Hoffman (1983) GENE 25, 263–269. The sequence of the genomic gene made it possible to design a PCR primer to catch the 5' part of the mRNA and at the same time introduce a Bam HI site right in front of the ATG start codon (NOR 2334). By using this primer at the 5' end and NOR 2153 again at the 3' end PCR was performed on the double stranded cDNA product. The full length coding part of the PCR-cDNA was then constructed by cloning the 5' Bam HI-Pvu I fragment from the PCR reaction together with the 3' Pvu I-Eco 0109, filled out with Klenow polymerase to make it blunt ended, into Bam HI-Nru I cut Aspergillus expression vector pToC 68 (FIG. 1), and the sequence of the inserted DNA was checked (pSX 320) (cf. FIG. 2). The sequence of the full length cDNA is SEQ ID NO:1.

formed as described in the published EP patent application No. 238 023. A number of transformants were screened for co-expression of ~43 kD endoglucanase. Transformants were evaluated by SDS-PAGE (p.3) and CMC endoglucanase activity.

The plasmid containing the genomic gene (pCaHj 109) was transformed into *Aspergillus oryzae* A1560-T40 by the same procedure. Evaluation of the transformants showed that the level of expression was similar to that of the cDNA transformants.

The purified ~43 kD endoglucanase was analysed for its N-terminal sequence and carbohydrate content. The N-terminal amino acid sequence was shown to be identical to that of the HPLC purified ~43 kD endoglucanase. The carbohydrate content differs from that of the HPLC purified ~43 kD enzyme in that the recombinant enzyme contains 10±8 galactose sugars per mol rather than glucose.

Example 3

Isolation of *Fusarium oxysporum* Genomic DNA

A freeze-dried culture of *Fusarium oxysporum* was reconstituted with phosphate buffer, spotted 5 times on each of 5 FOX medium plates (6% yeast extract, 1.5% $K_2HPO_4$, 0.75% $MgSO_4$ $7H_2O$, 22.5% glucose, 1.5% agar, pH 5.6) and incubated at 37° C. After 6 days of incubation the

```
Oligonucleotide primers used:
NOR 1251: 5'- AAYGCYGACAAAYCC -3'              (SEQ ID NO:9)

NOR 2048: 5'- AACGAYGAYGGNAAYTTCCC -3'         (SEQ ID NO:10)

NOR 2050: 5'- AAYGAYTGGTACDAYCARTG -3'         (SEQ ID NO:11)

NOR 2153: 5'- GCGCCAGTAGCAGCCGGGCTTGAGGG -3'   (SEQ ID NO:12)

NOR 2334: 5'- ACGTCTCAACTCGGATCCAAGATGCGTT -3' (SEQ ID NO:13)
                          Bam HI

NOR 2378: 5'- CTCAACTCTGATCAAGATGCGTTCC -3'    (SEQ ID NO:14)
                      Bcl I

NOR 2389: 5'- TGTCGACCAGTAAGGCCCTCAAGCTG -3'   (SEQ ID NO:15)
                 Sal I

Nomenclature:
Y: Pyrimidine (C+T)
R: Purine (A+G)
N: All four bases
Enhanced: Changes or insertions relative to original sequence.
Underlined: Restriction site introduced by PCR.
```

Expression of the ~43 kD Endoglucanase

The plasmid pSX 320 was transformed into *Aspergillus oryzae* A1560-T40, a protease deficient derivative of *A. oryzae* IFO 4177, using selection on acetamide by cotransformation with pToC 90 harboring the amdS gene from *A. nidulans* as a 2.7 kb Xba I fragment (Corrick et al. (1987), GENE 53, 63–71) on a pUC 19 vector (Yannisch-Perron et al. (1985), GENE 33, 103–119). Transformation was per-colonies were scraped from the plates into 15 ml of 0.001% Tween-80 which resulted in a thick and cloudy suspension.

Four 1-liter flasks, each containing 300 ml of liquid FOX medium, were inoculated with 2 ml of the spore suspension and were incubated at 30° C. and 240 rpm. On the 4th day of incubation, the cultures were filtered through 4 layers of sterile gauze and washed with sterile water. The mycelia were dried on Whatman filter paper, frozen in liquid nitrogen, ground into a fine powder in a cold morter and added to 75 ml of fresh lysis buffer (10 mM Tris-Cl 7.4, 1% SDS, 50 mM EDTA, 100 μl DEPC). The thoroughly mixed suspension was incubated in a 65° C. waterbath for 1 hour and then spun for 10 minutes at 4000 RPM and 5° C. in a bench-top centrifuge. The supernatant was decanted and EtOH precipitated. After 1 hour on ice the solution was spun at 19,000 rpm for 20 minutes. The supernatant was decanted and isopropanol precipitated. Following centrifugation at 10,000 rpm for 10 minutes, the supernatant was decanted and the pellets allowed to dry.

One milliliter of TER solution (10 mM Tris-HCl, pH 7.4, 1 mM EDTA 2000 100 μg RNAseA) was added to each tube, and the tubes were stored at 4° C. for two days. The tubes were pooled and placed in a 65° C. waterbath for 30 minutes to suspend non-dissolved DNA. The solution was extracted twice with phenol/CHCl₃/isoamyl alcohol, twice with CHCl₃/isoamyl alcohol and then ethanol precipitated. The pellet was allowed to settle and the EtOH was removed. 70% EtOH was added and the DNA was stored overnight at −20° C. After decanting and drying, 1 ml of TER was added and the DNA was dissolved by incubating the tubes at 65° C. for 1 hour. The preparation yielded 1.5 mg of genomic DNA.

Cloning of *Fusarium oxysporum* ~43 kD endoglucanase

To isolate the Fusarium homologue to the Humicola ~43 kD endoglucanase, a fragment was first obtained by PCR (as described IN U.S. Pat. No. 4,683,195 and U.S. Pat. No. 4,683,202) and cloned. This product was then sequenced and primers to be used as library probes and for PCR amplification were constructed. These oligonucleotides were used to isolate the corresponding clone from a cDNA library.

PCR was used to isolate partial length cDNA and genomic fragments of the 43 kD homologue. Seven different combinations of highly degenerate oligonucleotides (see table below) were used in PCR reactions with either cDNA or genomic DNA as templates. Only one combination yielded partial clones of the Fusarium 43 kd homologue. Two separate sets of PCR conditions were used for each oligonucleotide pair; the first set was designed to make very little product but with very high specificity. Various factors ensured specificity in this set of 28 cycles: The annealing temperature of 65° C. was very high for these oligonucleotides; the time at annealing temperature was set for only 30 seconds; 20 picomoles of each degenerate primer mixture was used per 100 μl reaction. The oligonucleotides used contained only the degenerate region without a "cloning element"; 1 unit of Amplitaq™ polymerase (Perkin-Elmer Cetus) was used per 100 μl reaction; and EDTA was added to reaction tubes at the end of the final 10 minute 72° C. incubation to prevent extension from mismatched primers at cooler temperatures following the PCR cycles. Products of the first set of cycles would not be expected to be visible by ethidium bromide staining in agarose gel electrophoresis due to the low efficiency of amplification required to ensure high specificity. The second set of amplifications was, however, designed to efficiently amplify products from the first set. Factors ensuring this include: lowering the annealing temperature to 55° C.; lengthening the time of annealing to 1 minute; increasing the amount of oligonucleotides to 100 picomoles of each mixture per 100 μl reaction; utilizing a different set of oligonucleotides which include a "Prime" cloning element along with the degenerate portion (increasing the melting melting temperature dramatically) and by using 2.5 units of Amplitaq polymerase per 100 μl reaction.

PCR reactions were set up as recommended by Perkin-Elmer Cetus. A master mix was made for each of 2 DNA sources, genomic and cDNA. This was comprised of 1× PCR buffer (10 mM Tris/HCl pH 8.3, 50 mM KCl, 1.5 mM MgCl₂, 0.01% gelatin, Perkin-Elmer Cetus), 0.2 mM deoxynucleotides (Ultrapure™ dNTP 100 mM solution, Pharmacia), 1 unit Amplitaq™ polymerase (Perkin Elmer Cetus) and 0.5 μg genomic DNA or 50 ng cDNA per 100 μl reaction mixture volume, and deionized water to bring volume up to 98 μl per 100 μl reaction. To labeled 0.5 tubes (Eppendorf) were added 20 picomoles (1 μl of a 20 picomole/μl concentration) of each oligonucleotide mixture (see table below). These were placed in a Perkin-Elmer Cetus thermocycler at 75° C. along with the master mixes and light mineral oil also in 0.5 ml tubes. Ninety eight microliters of the appropriate master mix and 55 μl light mineral oil were added to each tube with oligonucleotides. The reactions were then started in a step-cycle file (see chart below for parameters). At the end of the final 72° C. incubation, 50 μl of a 10 mM EDTA pH 8.0 solution was added to each tube and incubated for a further 5 minutes at 72° C.

Table of oligonucleotide pairs used in 43 kD homologue PCR:

| reaction | | | oligos for second set | expected size in de- |
|---|---|---|---|---|
| cDNA with | genomic base | oligos for first set | degenerate only "prime" | generate pairs |
| 1 | 11 | ZC3485 vs ZC3558 | ZC3486 vs ZC3559 | 288 |
| 2 | 12 | ZC3485 vs ZC3560 | ZC3486 vs ZC3561 | 510 |
| 3 | 13 | ZC3485 vs ZC3264 | ZC3486 vs ZC3254 | 756 |
| 4 | 14 | ZC3556 vs ZC3560 | ZC3557 vs ZC3561 | 159 |
| 5 | 15 | ZC3556 vs ZC3264 | ZC3557 vs ZC3254 | 405 |
| 6 | 16 | ZC3556 vs ZC3465 | ZC3557 vs ZC3466 | 405 |
| 7 | 17 | ZC3485 vs ZC3465 | ZC3486 vs ZC3466 | 756 |

Note: See oligonucleotide table for oligonucleotide sequences

Conditions for PCR step-cycle file were:

| SET 1: | | | SET 2: | | |
|---|---|---|---|---|---|
| 28 × | 94° C. | 1 min | 28 × | 94° C. | 1 min |
| | 65° C. | 30 sec | | 55° C. | 1 min |
| | 72° C. | 2 min | | 72° C. | 2 min |
| | 72° C. | 10 min | | 72° C. | 10 min |

Following the first set of PCR cycles, DNA was purified from the reaction mixtures by isopropyl alcohol precipitation for use in the second set of cycles. Most of the light mineral oil was removed from the top of each sample before transferring the sample to a new labeled tube. Each tube was then extracted with an equal volume PCI (49% phenol: 49% chloroform: 2% isoamyl alcohol) and then with an equal volume of chloroform. DNA was then precipitated from the reactions by adding: 75 μl 7.5 M ammonium acetate, 1 μl glycogen and 226 μl isopropyl alcohol. Pellets were resuspended in 20 μl deionized water. Two microliters of each resuspension were placed into labeled tubes for the second round of PCR amplifications along with 100 picomoles (5 μl of a 20 picomole/μl concentration ) of each new primer mixture (see table above). A master mix was made as described above except for excluding Alegenomic and cDNA templates and compensating for increased oligonucleotide and DNA volumes in the reaction tubes by decreasing the volume of water added. Reactions and cycles were set up as described above (see table above).

After the 28 cycles were completed, light mineral oil was removed from the tops of the samples, and the PCR mixtures were removed to new tubes. Ten microliters of each sample were spotted onto parafilm and incubated at 45° C. for approximately 5 minutes to allow the sample to decrease in volume and to allow the parafilm to absorb any residual light mineral oil. The drops were then combined with 2 μl 6× loading dye and electrophoresed on 1% agarose (Seakem GTG™, FMC, Rockland, Me.) gel. A single band of approximately 550 base pairs was found in reaction number 2 where the template was cDNA. A band of approximately 620 base pairs in reaction number 12 where the template was genomic DNA. These reactions were primed with oligonucleotides ZC3486 and ZC3561 (Table 1). This was very close to the 510 base pair PCR product predicted from comparison with the Humicola 43 kD sequence. The synthesis of a larger product in the reaction with genomic template is due to the presence of an intron within this region. The agarose containing these 2 bands was excised and DNA was extracted utilizing a Prep-A-Gene™ kit (BioRad) following manufacturers instructions. DNA was eluted with 50 μl deionized water and precipitated with 5 μl 3M sodium acetate, 1 μl glycogen and 140 μl ethanol. The DNA pellet was dried and resuspended in a volume of 7 μl TE (10 mM Tris-HCL pH 8.0, 1 mM EDTA).

The PCR fragments were cloned into pBS sk-'vector was constructed by first digesting pBluescript II sk- (Stratagene, La Jolla, Calif.) with Eco RI and gel purifying cut plasmid from 0.8% seaplaque GTG™ agarose (FMC) with a Pre-A-Gene™ kit (BioRad) following the manufacturer's instructions. Oligonucleotides ZC1773 and ZC1774 (Table 1) were anealed by mixing 2 picomoles of each oligonucleotide, bringing up the reaction volume to 4 μl with deionized water then adding 0.5 μl anealing buffer (200 mM Tris-HCl pH 7.6, 50 mM $MgCl_2$) and bringing the temperature up to 65° C. for 30 seconds and slowly cooling to 20° C. in 20 minutes in a Perkin-Elmer Cetus PCR thermocycler. The oligonucleotides were then ligated into the Eco RI digested pBluescript vector by mixing: 5.5 μl deionized water, 2 μl anealed oligonucleotides, 1 μl of a 1:3 dilution in deionized water of digested vector, 1 μl 10× T4 DNA ligase buffer (Boehringer-Mannheim Biochemicals, Indianapolis Ind.) and 0.5 T4 DNA ligase (Gibco-BRL), and incubating the mixture at 16° C. for 2.5 hours. The ligation mixture was then brought up to a volume of 100 μl with deionized water and extracted with PCI and chloroform. To increase electroporation efficiency, DNA was then precipitated with 50 μl ammonium acetate, 1 μl glycogen and 151 μl isopropanol. One microliter of a 10 μl resuspension in deionized water was electroporated into *E. coli* DH10-B electromax cells (Gibco-BRL) using manufacturer's instructions, in a Bio-Rad electroporation apparatus. Immediately following the electroporation, 1 ml of 2XYT (per liter: 16 g tryptone, 10 g yeast extract, 10 g NaCl) broth was added to the cuvet and mixed. Various dilutions were plated onto 100 mm LB plates (per liter: 10 g tryptone, 8 g yeast extract, 5 g NaCl, 14.5 g agar) with 100 μg/ml ampicillin, and coated with 100 μl of 20 mg/ml X-Gal (5-Bromo-4 Chloro-3-Indolyl-b-D-galactropyranoside; Sigma, St. Louis, Mo.) in dimethylformamide and 20 μl of 1M IPTG (Sigma). After overnight growth various blue and white colonies were analyzed by PCR for small inserts using the oligonucleotides ZC3424 (bluescript reverse primer) and ZC3425 (T7 promoter primer) (Table 1), following conditions outlined above for screening bacterial plugs. After an initial 1 minute 45 seconds at 94° C. denaturation, 30 cycles of 94° C. for 45 seconds, 40° for 30 seconds and 72° C. for 1 minute were performed. Upon agarose gel electrophoresis of the PCR products, 1 blue colony giving a PCR band consistant with a small insert in the pBluescript cloning region was chosen for DNA purification and was grown up overnight in a 100 ml liquid culture in TB (per liter: 12 g tryptone, 24 g yeast extract, 4 ml glycerol, autoclave. Then add 100 ml of 0.17M $KH_2PO_4$, 0.72M $K_2HPO_4$; Sambrook et al., Molecular Cloning, 2nd Ed., 1989, A.2) with 150 μg/ml ampicillin. DNA was isolated by alkaline lysis and PEG precipitation (Sambrook et al., Molecular Cloning 2nd ed., 1.38–1.41, 1989). Sequence analysis showed the correct oligonucleotide to be inserted while maintaining the β-galactosidase gene present in pBluescript vectors in frame with the promoter. Fifty micrograms of the DNA preparation was digested with Eco RI, PCI and chloroform extracted, and precipitated with sodium acetate and ethanol. The DNA pellet was resuspended in 50 μl deionized water. Digested pBS sk-' was cut back with T4 DNA polymerase (Gibco-BRL) by adding 40 μl 10×T4 DNA polymerase buffer (0.33M Tri/acetate pH 8.0, 0.66M potassium acetate, 0.1M magnesium acetate, 5 mM dithiotheretiol, 5 mM BSA (New England Biolabs) 260 μl deionized water, 40 μl 1 mM dTTP (Ultrapure™, Pharmacia) and 40 μl T4 DNA polymerase (1 U/μl) (Gibco-BRL) to 20 μl of 1 mg/ml vector DNA. The mixture was incubated at 12° C. for 15 minutes, then at 75° C. for 10 minutes. To prepare the DNA for use in ligation, it was PCI and chloroform extracted and precipitated with sodium acetate and ethanol. The pellet was resuspended in 200 μl deionized water, producing a concentration of 0.1 μg/μl.

To prepare the 43 kd homologue PCR products for insertion into the cut-back pBS sk-' vector, they were cut back with T4 DNA polymerase (Gibco-BRL) in reaction volumes of 10 μl with the inclusion of dATP instead of dTTP. The resulting DNA solutions were PCI and chloroform extracted and precipitated with sodium acetate, glycogen and ethanol. The DNA pellets were resuspended in 15 μl deionized water. DNA samples of 7.5 μl were ligated into 0.1 μg cut back pBS sk-' (0.1 μg/μl) with 1 μl 10× ligase buffer (Boehringer-Mannheim) and 0.5 μl of $T_4DNA$ ligase (Boehringer-Mannheim). The ligation mixtures were then brought up to a volume of 150 μl with deionized water and extracted with PCI and chloroform. To increase electroporatoin efficiency, DNA was then precipitated with 15 μl sodium acetate, 1 μl glycogen and 166 μl isopropanol. One microliter of a 10 μl resuspension in deionized water was electroporated into *E. coli* DH10-B electromax cells (BRL) using a Bio-Rad electroporation apparatus, according to manufacturer's instructions. Immediately following the electroporation, 1 ml of SOB broth (per liter: 20 g tryptone, 5 g yeast extract, 10 ml 1M NaCl, 2.5 ml 1M KCl. Autoclave then add 10 ml 1 M $MgCl_2$ and 10 ml 1M $MgSO_4$) was added to the cuvet, and the cell mixture was transferred to a 100 mm tube and incubated at 37° C. for 1 hour with airation. Various dilutions were plated onto 100 mm LB plates containing 100 μg/ml ampicillin and coated with 100 μl of 20 mg/ml X-Gal (Sigma) in dimethylformamide and 20 μl of 1M IPTG (Sigma). Three white colonies of each of the 2 transformations, cDNA and genomic, were picked for sequencing. Sequence analysis showed the inserts to be highly homologous to the Humicola 43 kD cellulase. The genomic insert was identical to the cDNA except for the presence of an intron. Two 42-mer ologonucleotides ZC3709 and ZC3710 (Table 1) were designed from the sequence for use as library probes and PCR primers. The oligonucleotides were from opposite ends of the PCR product and were designed to hybridize opposite strands of the DNA so that they could be used as primers in a PCR reaction to test potential clones in the library screening.

Construction of a *Fusarium oxysporum* cDNA Library

*Fusarium oxysporum* was grown by fermentation and samples were withdrawn at various times for RNA extraction and cellulase activity analysis. The activity analysis included an assay for total cellulase activity as well as one for colour clarification. *Fusarium oxysporum* samples demonstrating maximal colour clarification were extracted for total RNA from which poly(A)+RNA was isolated.

To construct a *Fusarium oxysporum* cDNA library, first-strand cDNA was synthesized in two reactions, one with and the other without radiolabelled dATP. A 2.5× reaction mixture was prepared at room temperature by mixing the following reagents in the following order: 10 μl of 5× reverse transcriptase buffer (Gibco-BRL, Gaithersburg, Md.) 2.5 μl 200 mM dithiothreitol (made fresh or from a stock solution stored at −70° C.), and 2.5 μl of a mixture containing 10 mM of each deoxynucleotide triphosphate, (dATP, dGTP, dTTP and 5-methyl dCTP, obtained from Pharmacia LKB Biotechnology, Alameda, Calif.). The reaction mixture was divided into each of two tubes of 7.5 μl. 1.3 μl of 10 μCi/μl $^{32p}$ α-dATP (Amersham, Arlington Heights, Ill.) was added to one tube and 1.3 μl of water to the other. Seven microliters of each mixture was transferred to final reaction tubes. In a separate tube, 5 μg of *Fusarium oxysporum* poly $(A)^+$ RNA in 14 μl of 5 mM Tris-HCl pH 7.4, 50 μM EDTA was mixed with 2 μl of 1 μg/μl first strand primer (ZC2938 $GACAGAGCACAGAATTCACTAGTGAGCTCT_{15}$)(SEQ ID NO:16). The RNA-primer mixture was heated at 65° C. for 4 minutes, chilled in ice water, and centrifuged briefly in a microfuge. Eight microliters of the RNA-primer mixture was added to the final reaction tubes. Five microliters of 200 U/μl Superscript™ reverse transcriptase (Gibco-BRL) was added to each tube. After gentle agitation, the tubes were incubated at 45° C. for 30 minutes. Eighty microliters of 10 mM Tris-HCl pH 7.4, 1 mM EDTA was added to each tube, the samples were vortexed, and briefly centrifuged. Three microliters was removed from each tube to determine counts incorporated by TCA precipitation and the total counts in the reaction. A 2 μl sample from each tube was analyzed by gel electrophoresis. The remainder of each sample was ethanol precipitated in the presence of oyster glycogen. The nucleic acids were pelleted by centrifugation, and the pellets were washed with 80% ethanol. Following the ethanol wash, the samples were air dried for 10 minutes. The first strand synthesis yielded 1.6 μg of *Fusarium oxysporum* cDNA, a 33% conversion of poly(A)+RNA into DNA.

Second strand cDNA synthesis was performed on the RNA-DNA hybrid from the first strand reactions under conditions which encouraged first strand priming of second strand synthesis resulting in hairpin DNA. The first strand products from each of the two first strand reactions were resuspended in 71 μl of water. The following reagents were added, at room temperature, to the reaction tubes: 20 μl of 5× second strand buffer (100 mM Tris pH 7.4, 450 mM KCl, 23 mM $MgCl_2$, and 50 mM $(NH_4)_2(SO_4)$, 3 μl of 5 mM β-NAD, and μl of a deoxynucleotide triphosphate mixture with each at 10 mM. One microliter of α-$^{32p}$ dATP was added to the reaction mixture which received unlabeled dATP for the first strand synthesis while the tube which received labeled dATP for first strand synthesis received 1 μl of water. Each tube then received 0.6 μl of 7 U/μl *E. coli* DNA ligase (Boehringer-Mannheim, Indianapolis, Ind.), 3.1 μl of 8 U/μl *E. coli* DNA polymerase I (Amersham), and 1 μl 2 U/μl of RNase H (Gibco-BRL). The reactions were incubated at 16° C. for 2 hours. After incubation, 2 μl from each reaction was used to determine TCA precipitable counts and total counts in the reaction, and 2 μl from each reaction was analyzed by gel electrophoresis. To the remainder of each sample, 2 μl of 2.5 μg/μl oyster glycogen, 5 μl of 0.5 EDTA and 200 μl of 10 mM Tris-HCl pH 7.4, 1 mM EDTA were added. The samples were phenol-chloroform extracted and isopropanol precipitated. After centrifugation the pellets were washed with 100 μl of 80% ethanol and air dried. The yield of double stranded cDNA in each of the reactions was approximately 2.5 μg.

Mung bean nuclease treatment was used to clip the single-stranded DNA of the hair-pin. Each cDNA pellet was resuspended in 15 μl of water and 2.5 μl of 10× mung bean buffer (0.3 M NaAc pH 4.6, 3 M NaCl, and 10 mM $ZnSO_4$), 2.5 μl of 10 mM DTT, 2.5 μl of 50% glycerol, and 2.5 μl of 10 U/μl mung bean nuclease (New England Biolabs, Beverly, Mass.) were added to each tube. The reactions were incubated at 30° C. for 30 minutes and 75 μl of 10 mM Tris-HCl pH 7.4 and 1 mM EDTA was added to each tube. Two-microliter aliquots were analyzed by alkaline agarose gel analysis. One hundred microliters of 1 M Tris-HCl pH 7.4 was added to each tube and the samples were phenol-chloroform extracted twice. The DNA was isopropanol precipitated and pelleted by centrifugation. After centrifugation, the DNA pellet was washed with 80% ethanol and air dried. The yield was approximately 2 μg of DNA from each of the two reactions.

The cDNA ends were blunted by treatment with T4 DNA polymerase. DNA from the two samples were combined after resuspension in a total volume of 24 μl of water. Four microliters of 10× T4 buffer (330 mM Tris-acetate pH 7.9, 670 mM KAc, 100 mM MgAc, and 1 mg/ml gelatin), 4 μl of 1 mM dNTP, 4 μl 50 mM DTT, and 4 μl of 1 U/μl T4 DNA polymerase (Boehringer-Mannheim) were added to the DNA. The samples were incubated at 15° C. for 1 hour. After incubation, 160 μl of 10 mM Tris-HCl pH 7.4, 1 mM EDTA was added, and the sample was phenol-chloroform extracted. The DNA was isopropanol precipitated and pelleted by centrifugation. After centrifugation the DNA was washed with 80% ethanol and air dried.

After resuspension of the DNA in 6.5 μl water, Eco RI adapters were added to the blunted DNA. One microliter of 1 μg/μl Eco RI adapter (Invitrogen, San Diego, Calif. Cat. # N409–20), 1 μl of 10× ligase buffer (0.5 M Tris pH 7.8 and 50 mM $MgCl_2$), 0.5 μl of 10 mM ATP, 0.5 μl of 100 mM DTT, and 1 μl of 1 U/μl T4 DNA ligase (Boehringer-Mannheim) were added to the DNA. After the sample was incubated overnight at room temperature, the ligase was heat denatured at 65° C. for 15 minutes.

The Sst I cloning site encoded by the first strand primer was exposed by digestion with Sst I endonuclease. Thirty-three microliters of water, 5 μl of 10× Sst I buffer (0.5 M Tris pH 8.0, 0.1 M $MgCl_2$, and 0.5 M NaCl), and 2 μl of 5 U/μl Sst I were added to the DNA, and the samples were incubated at 37° C. for 2 hours. One hundred and fifty microliters of 10 mM Tris-HCl pH 7.4, 1 mM EDTA was added, the sample was phenol-chloroform extracted, and the DNA was isopropanol precipitated.

The cDNA was chromatographed on a Sepharose CL 2B (Pharmacia LKB Biotechnology) column to size-select the cDNA and to remove free adapters. A 1.1 ml column of Sepharose CL 2B was poured into a 1 ml plastic disposable pipet and the column was washed with 50 column volumes of buffer (10 mM Tris pH 7.4 and 1 mM EDTA). The sample was applied, one-drop fractions were collected, and the DNA in the void volume was pooled. The fractionated DNA was isopropanol precipitated. After centrifugation the DNA was washed with 80% ethanol and air dried.

A *Fusarium oxysporum* cDNA library was established by ligating the cDNA to the vector pYcDE8' (cf. WO 90/10698) which had been digested with Eco RI and Sst I. Three hundred and ninety nanograms of vector was ligated to 400 ng of cDNA in a 80 μl ligation reaction containing 8 μl of 10 × ligase buffer, 4 μl of 10 mM ATP, 4 μl 200 mM DTT, and 1 unit of T4 DNA ligase (Boehringer-Mannheim. After overnight incubation at room temperature, 5 μg of oyster glycogen and 120 μl of 10 mM Tris-HCl and 1 mM EDTA were added and the sample was phenol-chloroform extracted. The DNA was ethanol precipitated, centrifuged, and the DNA pellet washed with 80% ethanol. After air drying, the DNA was resuspended in 3 μl of water. Thirty seven microliters of electroporation competent DH10B cells (Gibco-BRL) was added to the DNA, and electroporation was completed with a Bio-Rad Gene Pulser (Model #1652076) and BioRad Pulse Controller (Model #1652098) electroporation unit (Bio-Rad Laboratories, Richmond, Calif.). Four milliliters of SOC (Hanahan, J. Mol. Biol. 166 (1983), 557–580) was added to the electroporated cells, and 400 μl of the cell suspension was spread on each of ten 150 mm LB amipicillin plates. After an overnight incubation, 10 ml of LB amp media was added to each plate, and the cells were scraped into the media. Glycerol stocks and plasmid preparations were made from each plate. The library background (vector without insert) was established at aproximately 1% by ligating the vector without insert and titering the number of clones after electroporation.

To isolate full length cDNA clones of the 43 kD homologue a library of 1,100,000 clones was plated out onto 150 mm LB plates with 100 μg/ml ampicillin. One hundred thousand clones were plated out from glycerol stocks onto each of 10 plates and 20,000 clones were plated out on each of 5 plates. Lifts were taken in duplicate as described above. Prehydridization, hybridization and washing were also carried out as described above. Two end labeled 42-mer oligonucleotides, ZC3709 and ZC3710 (which are specific for the 43 kD homologue), were used in the hybridization. Filters were washed once for 20 minutes with TMACL at 77° C. Twenty two spots showing up on duplicate filters were found. Corresponding areas on the plates were picked with the large end of a pipet into 1 ml of 1× PCR buffer. These isolated analyses by PCR were with 2 sets of oligonucleotides for each isolate. One set contained the two 43 kD specific oligonucleotides used as hybridization probes and the other contained one 43 kD specific oligonucleotide, ZC3709, and one vector specific oligonucleotide, ZC3634. PCR was conducted as before by Perkin Elmer Cetus directions. Twenty picomoles of each primer and 5 μl of the cell suspension were used in each reaction of 50 μl. After an initial 1 minute 30 second denaturation at 94° C. 30 cycles of 1 minute at 94° C. and 2 minutes at 72° C. were employed, with a final extension time of 10 minutes at 72° C. Results showed 17 of the 22 to contain the 2 43 kD specific oligonucleotide recognition sites. The remaining 5 clones contained one of the 2 sites, ZC3709, but were shown by PCR with the vector specific primer to be truncated and not long enough to contain the other site. The 9 longest clones were chosen for single colony isolation through another level of screening. Five 10 fold dilutions of each were plated out and processed as described above for the first set of lifts. All of the nine had signals on autoradiograms of the second level of screening. Colonies were fairly congested so a few separate colonies in the area of the radioactive signal were single colony isolated on 150 mm LB plates with 70 μg/ml ampicillin. These were tested by PCR for homologues to the ~43 kD endoglucanase with the oligonucleotides ZC3709 and ZC3710 as described for the first level of screening except that colonies were picked by toothpick into 25 μl of mastermix. Bands of the expected size were obtained for 7 of the 9 clones. Cultures of these were started in 20 ml of Terrific Broth with 150 μg/ml ampicillin. DNA was isolated by alkaline lysis and PEG precipitation as above.

DNA Sequence Analysis

The cDNAs were sequenced in the yeast expression vector pYCDE8'. The dideoxy chain termination method (F. Sanger et al., *Proc. Natl. Acad. Sci. USA* 74, 1977, pp. 5463–5467) using @35-S dATP from New England Nuclear (cf. M. D. Biggin et al., *Proc. Natl. Acad. Sci. USA* 80, 1983, pp. 3963–3965) was used for all sequencing reactions. The reactions were catalysed by modified t7 DNA polymerase from Pharmacia (cf. S. Tabor and C. C. Richardson, *Proc. Natl. Acad. Sci. USA* 84, 1987, pp. 4767–4771) and were primed with an oligonucleotide complementary to the ADH1 promoter (ZC996: ATT GTT CTC GTT CCC TTT CTT), complementary to the CYC1 terminator (ZC3635: TGT ACG CAT GTA ACA TTA) or with oligonucleotides complementary to the DNA of interest. Double stranded templates were denatured with NaOH (E. Y. Chen and P. H. Seeburg, *DNA* 4, 1985, pp. 165–170) prior to hybridizing with a sequencing oligonucleotide. Oligonucleotides were synthesized on an Applied Biosystems Model 380A DNA synthesizer. The oligonucleotides used for the sequencing reactions are listed in the sequencing oligonucleotide table below:

TABLE 1

Oligonucleotides for 43 kD homologue PCR:

| | |
|---|---|
| ZC3485 TGG GA(C/T) TG(C/T) TG(C/T) AA(A/G) CC | (SEQ ID NO: 17) |
| ZC3486 AGG GAG ACC GGA ATT CTG GGA (C/T)TG (C/T)TG (C/T) AA(A/G) CC | (SEQ ID NO: 18) |
| ZC3556 CC(A/C/G/T) GG(A/C/G/T) GG(A/C/G/T) GG(A/C/G/T) GT(A/C/G/T) GG | (SEQ ID NO: 19) |
| ZC3557 AGG GAG ACC GGA ATT CCC (A/C/G/T)GG (A/C/G/T)GG (A/C/G/T)GG (A/C/G/T)GT (A/C/G/T)GG | (SEQ ID NO: 20) |
| ZC3558 AC(A/C/G/T) A(C/T)C AT(A/C/G/T) (G/T)T/C/T) TT(A/C/G/T) CC | (SEQ ID NO: 21) |
| ZC3559 GAC AGA GCA CAG AAT TCA C(A/C/G/T)A (C/T)CA T(A/C/G/T)(G/T) T(C/T)T T(A/C/G/T)C C | (SEQ ID NO: 22) |

TABLE 1-continued

```
ZC3560 (A/C/G/T)GG (A/G)TT (A/G)TC (A/C/G/T)GC           (SEQ ID NO: 23)
       (A/C/G/T)(G/T)(C/T) (C/T)T(C/T) (A/G)AA CCA

ZC3561 GAC AGA GCA CAG AAT TC(A/C/G/T) GG(A/G) TT(A/G)  (SEQ ID NO: 24)
       TC(A/C/G/T) GC(A/C/G/T) (G/T)(C/T)(C/T) T(C/T)(A/G)
       AAC CA
Oligonucleotides for 43 kD homologue cloning:

ZC3709 GGG GTA GCT ATC ACA TTC GCT TCG GGA GGA GAT ACC GCC  (SEQ ID NO: 25)
       GTA

ZC3710 CTT CTT GCT CTT GGA GCG GAA AGG CTG CTG TCA ACG CCC  (SEQ ID NO: 26)
       CTG
pYCDE8' vector oligonucleotides:

ZC3635 TGT ACG CAT GTA ACA TTA                          (SEQ ID NO: 27)  CYC 1 terminator ZC3634 CTG CAC AAT ATT TCA AGC                          (SEQ ID NO: 28)  ADH 1 promoter
43kD homologue specific sequencing primers:

ZC3709 GGG GTA GCT ATC ACA TTC GCT TCG GGA GGA GAT ACC GCC GTA  (SEQ ID NO: 29)

ZC3710 CTT CTT GCT CTT GGA GCG GAA AGG CTG CTG TCA ACG CCC CTG  (SEQ ID NO: 30)

ZC3870 AGC TTC TCA AGG ACG GTT                          (SEQ ID NO: 31)

ZC3881 AAC AAG GGT CGA ACA CTT                          (SEQ ID NO: 32)

ZC3882 CCA GAA GAC CAA GGA TT                           (SEQ ID NO: 33)
```

Example 4

Colour Clarification Test

The Humicola ~43 kD endoglucanase (a mixture of 30 purification runs) was compared in a colour clarification test with the *H. insolens* cellulase preparation described in U.S. Pat. No. 4,435,307, Example 6.

Old worn black cotton swatches are used as the test material. The clarification test is made in a Terg-O-tometer making three repeated washes. Between each wash the swatches are dried overnight.

Conditions 2 g/l of liquid detergent at 40° C. for 30 min. and a water hardness of 9° dH. The swatch size is 10×15 cm, and there are two swatches in each beaker.

The composition of the detergent was as follows:

10% anionic surfactant (Nansa 1169/p)

15% non-ionic surfactant (Berol 160)

10% ethanol

5% triethanol amine

60% water 30 pH adjusted to 8.0 with HCl.

Dosage

The two enzymes are dosed in 63 and 125 CMC-endoase units/l.

Results

The results were evaluted by a panel of 22 persons who rated the swatches on a scale from 1 to 7 points. The higher the score, the more colour clarification obtained.

| Enzyme | CMC-endoase/l | Protein mg/l | PSU* |
|---|---|---|---|
| No enzyme | | | 1.4 ± 1.0 |
| *H. insolens* | 63 | 14 | 5.8 ± 1.0 |
| cellulase mixture | 125 | 28 | 6.1 ± 1.0 |
| Invention | 63 | 0.4 | 4.6 ± 0.9 |
| | 125 | 0.8 | 6.2 ± 0.8 |

*PSU = Panel Score Units

The ~43 kD endoglucanase is shown to have an about 30 times better performance than the prior art *H. insolens* cellulase mixture and an about 6 times better performance than the cellulase preparation according to WO 89/09259.

Example 5

Stability of the Humicola ~43 kD Endoglucanase in the Presence of Proteases

The storage stability of the ~43 kD endoglucanase in liquid detergent in the presence of different proteases was determined under the following conditions:

Enzymes

~43 kD endoglucanase of the invention

Glu/Asp specific *B. licheniformis* serine protease

Trypsin-like *Fusarium* sp. DSM 2672 protease

*B. lentus* serine protease

Subtilisin Novo

Detergent

US commercial liquid detergent not containing any opacifier, perfume or enzymes (apart from those added in the experiment). ±1% (w/w) boric acid as enzyme stabiliser.

Dosage

Endoglucanase: 12 CMCU/g of detergent

Proteases: 0.2 mg/g of detergent

Incubation 7 days at 35° C.

Residual Activity

The residual activity of the endoglucanase after 7 days of incubation with the respective proteases was determined in terms of its CMCase activity (CMCU).

The CMCase activity was determined as follows:

A substrate solution of 30 g/l CMC (Hercules 7 LFD) in deionized water was prepared. The enzyme sample to be determined was dissolved in 0.01 M phosphate buffer, pH 7.5. 1.0 ml of the enzyme solution and 2.0 ml of a 0.1 M phosphate buffer, pH 7.5, were mixed in a test tube, and an enzyme reaction was initiated by adding 1.0 ml of the substrate solution to the test tube. The mixture was incubated at 40° C. for 20 minutes, after which the reaction was stopped by adding 2.0 ml of 0.125 M trisodium phosphate.12H$_2$O. A blind sample was prepared without incubation.

2.0 ml of a ferricyanide solution (1.60 g of potassium ferricyanide and 14.0 g of trisodium phosphate.12H$_2$O in 1 l of deionized water) was added to a test sample as well as to a blind immediately followed by immersion in boiling water and incubation for 10 minutes. After incubation, the samples were cooled with tap water. The absorbance at 420 nm was measured, and a standard curve was prepared with glucose solution.

One CMCase unit (CMCU) is defined as the amount of enzyme which, under the conditions specified above, forms an amount of reducing carbohydrates corresponding to 1 μmol of glucose per minute.

Results

The storage stability of the endoglucanase of the invention was determined as its residual activity (in CMCU %) under the conditions indicated above.

| Protease | Residual Activity (%) | |
| --- | --- | --- |
|  | +boric acid | −boric acid |
| Glu/Asp specific | 105 | 93 |
| Trypsin-like | 77 | 63 |
| B. lentus serine | 57 | 24 |
| Subtilisin Novo | 63 | 55 |

These results indicate that the storage stability in liquid detergent of the endoglucanase of the invention is improved when a protease with a higher degree of specificity than Savinase is included in the detergent composition.

Example 6

Use of Humicola ~43 kD Endoglucanase to Provide a Localized Variation in Colour of Denim Fabric Denim jeans were subjected to treatment with the ~43 kD endoglucanase in a 12 kg "Wascator" FL120 wash extractor with a view to imparting a localized variation in the surface colour of the jeans approximating a "stonewashed" appearance.

Four pairs of jeans were used per machine load. The experimental conditions were as follows.

Desizing
    40 l water
    100 ml B. amyloliquefaciens amylase*, 120 L
    70 g KH$_2$PO$_4$
    30 g Na$_2$HPO$_4$
    55° C.
    10 minutes
    pH 6.8
*available from Novo Nordisk A/S.

The desizing process was followed by draining.

Abrasion
    40 l water
    120 g H. insolens cellulase mixture or x g ~43 kD endoglucanase
    70 g KH$_2$PO$_4$
    30 g Na$_2$HPO$_4$
    55° C.
    75 minutes
    pH 6.6

The abrasion process was followed by draining, rinsing, after-washing and rinsing.

The results were evaluated by judging the visual appearance of the jeans.

Different dosages of ~43 kD endoglucanase were used to obtain an abrasion level which was equivalent to that obtained with 120 g H. insolens cellulase mixture. Such an equivalent level was obtained with 1.0–1.25 g of ~43 kD endoglucanase. Measurements of the tear strength of the treated garments showed no significant difference between the two enzyme treatments.

Example 7

Use of Humicola ~43 kD Endoglucanase to Remove Fuzz from Fabric Surface

Woven, 100% cotton fabric was treated with the ~43 kD endoglucanase in a 12 kg "Wascator" FL120 wash extractor with a view to investigating the ability of the enzyme to impart a greater degree of softness to new fabric.

The experimental conditions were as follows.

Fabric

Woven, 100% cotton fabric obtained from Nordisk Textil, bleached (NT2116-b) or unbleached (NT2116-ub). 400 g of fabric were used per machine load.

Desizing
    40 l water
    200 ml B. amyloliquefaciens amylase, 120 L
    60 g KH$_2$PO$_4$
    20 g Na$_2$HPO$_4$
    60° C.
    10 minutes
    pH 6.4

The desizing process was followed by draining.

Main wash
    40 l water
    0–600 g H. insolens cellulase mixture or x g ~43 kD endoglucanase
    60 g KH$_2$PO$_4$
    40 g Na$_2$HPO$_4$
    60° C.
    60 minutes
    pH 6.7

The abrasion step was followed by draining.

Afterwash
    40 l water
    40 g Na$_2$CO$_3$
    10 g Berol 08
    80° C.
    15 minutes
    pH 10.1

The afterwash was followed rinsing.

Three different concentrations of the ~43 kD endoglucanase were added in the main wash.

The weight loss of the fabric samples was measured before and after treatment. The weight loss is expressed in % and is related to the desized fabric.

Fabric thickness was measured by means of a thickness measurer L&W, type 22/1. 2 swatches of the fabric (10×6 cm) were measured, and 5 measurements in $\mu$m were recorded for each swatch. The swatch was measured at a pressure of 98.07 kPa. The retained thickness is expressed in % in relation to the desized fabric.

Fabric strength was measured by means of a tearing tester (Elmendorf 09). 6 swatches (10×6 cm) were cut in the warp direction and 6 swatches (10×6 cm) in the weft direction. The tear strength was measured in mN in accordance with ASTM D 1424. The fabric strength of the enzyme-treated fabric is expressed in % in relation to the desized fabric.

Fabric stiffness was measured by means of a King Fabric Stiffness Tester. 4 swatches (10×20 cm; 10 cm in the warp direction) are cut from the fabric, and each swatch is folded back to back (10×10 cm) and placed on a table provided with an open ring in the middle. A piston pushes the fabric through the ring using a certain power expressed in grammes. The determination is made according to the ASTM D 4032 Circular Bend Test Method. Retained fabric stiffness is expressed in % in relation to the desized fabric.

The results of these tests appear from the following table:

| Enzyme Dosage EUG/l | Weight Loss % | Retained Thickness % | Retained Strength % | Retained Stiffness % |
|---|---|---|---|---|
| 0 | 0 | 100 | 100 | 100 |
| 13 | 4.0 | 95.3 | 85.4 | 88.6 |
| 50 | 5.1 | 94.5 | 73.3 | 85.0 |
| 150 | 7.7 | 91.9 | 70.7 | 79.3 |

Example 8

Use of Humicola ~43 kD Endoglucanase for the Treatment of Paper Pulp

The ~43 kD endoglucanase was used for the treatment of several types of paper pulp with a view to investigating the effect of the enzyme on pulp drainage.

The experimental conditions were as follows.

Pulps

1. Waste paper mixture: composed of 33% newsprint, 33% magazines and 33% computer paper. With or without deinking chemicals (WPC or WP, respectively)
2. Recycled cardboard containers (RCC).
3. Bleached kraft: made from pine (BK).
4. Unbleached thermomechanical: made from fir (TMP).

Determination of cellulase activity (CEVU)

A substrate solution containing 33.3 g/l CMC (Hercules 7 LFD) in Tris-buffer, pH 9.0, is prepared. The enzyme sample to be determined is dissolved in the same buffer. 10 ml substrate solution and 0.5 ml enzyme solution are mixed and transferred to a viscosimeter (Haake VT 181, NV sensor, 181 rpm) thermostated at 40° C. One Cellulase Viscosity Unit (CEVU) is defined in Novo Nordisk Analytical Method No. AF 253 (available from Novo Nordisk).

Determination of pulp drainage (Schopper-Riegler)

The Schopper-Riegler number (SR) is determined according to ISO standard 5267 (part 1) on a homogenous pulp with a consistency of 2 g/l. A known volume of pulp is allowed to drain through a metal sieve into a funnel. The funnel is provided with an axial hole and a side hole. The volume of filtrate that passes through the side hole is measured in a vessel graduated in Schopper-Riegler units.

Enzymatic treatment

A preparation of the ~43 kD endoglucanase was diluted to 7 CEVU/ml and added to each of the pulps indicated above (50 g DS, consistency 3%). The enzyme dose was 2400 CEVU/kg dry pulp. The enzymatic treatment was conducted at a pH of 7.5 and at 40° C. with gentle stirring for 60 minutes. A sample was taken after 30 minutes to monitor the progression of the reaction. After 60 minutes, the pulp was diluted to a consistency of 0.5% with cold water (+4° C.) in order to stop the reaction.

Drainage of the wet pulp was determined as described above and assigned Schopper-Riegler (SR) values. The drainage time (DT) under vacuum was also determined.

The results are summarized in the following table.

TABLE 3

Results of the drainage and strength measurements.
Control experiments. Same conditions as the enzyme treatment.

| | Control | Enzyme |
|---|---|---|
| | Waste paper + chemicals | |
| SR (3%) | 61 | 55 |
| Drainage time (s) | 18.2 | 17 |
| 150 g/m² | | |
| Mass g/m² | 65.6 | 66.4 |
| Vol cm³/g | 1.65 | 1.66 |
| Breaking Length, m | 3650 | 3970 |
| Burst Index | 2.19 | 2.47 |
| | Waste paper | |
| SR (3%) | 59 | 51 |
| Drainage time (s) | 18.2 | 12.7 |
| 150 g/m² | | |
| Mass g/m² | 68.0 | 67.9 |
| Vol cm³/g | 1.68 | 1.64 |
| Breaking Length, m | 3810 | 3790 |
| Burst Index | 2.25 | 2.33 |
| | Recycled Cardboard Containers | |
| SR (3%) | 45 | 33 |
| Drainage time (s) | 6.8 | 5.3 |
| 150 g/m² | | |
| Mass g/m² | 70.2 | 67.3 |
| Vol cm³/g | 1.91 | 1.99 |
| Breaking Length, m | 3640 | 3530 |
| Burst Index | 2.25 | 2.22 |
| | Kraft | |
| SR (3%) | 42 | 31 |
| Drainage time (s) | 10.7 | 6 |
| 150 g/m² | | |
| Mass g/m² | 67.5 | 69,1 |
| Vol cm³/g | 1.44 | 1.42 |
| Breaking Length, m | 7010 | 7190 |
| Burst Index | 5.14 | 4.96 |
| | TMP | |
| SR (3%) | 68 | 60 |
| Drainage time (s) | 13.8 | 11.3 |
| 150 g/m² | | |
| Mass g/m² | 68.7 | 70.2 |
| Vol cm³/g | 2.13 | 2.04 |
| Breaking Length, m | 3630 | 3620 |
| Burst Index | 1.95 | 1.91 |

It appears from the table that the ~43 kD endoglucanase treatment causes a significant decrease in SR values and significantly improves drainage of pulps used in papermaking.

Paper sheets were made from the various pulps on a Rapid Köthen device and measured for strength according to different parameters (including breaking length). No decrease in strength properties due to enzyme action was observed.

---

We claim:

1. An isolated enzyme exhibiting endoglucanase activity comprising amino acids 1–294 of SEQ ID NO:2.

2. An isolated enzyme exhibiting endoglucanase activity, wherein the enzyme is encoded by a nucleotide sequence from which sequence a polymerase chain reaction (PCR) fragment may be amplified by using a set of sense and antisense oligonucleotides primers selected from the group consisting of
   (a) sense primer SEQ ID NO:17 and antisense primer SEQ ID NO:21,
   (b) sense primer SEQ ID NO:18 and antisense primer SEQ ID NO:22,
   (c) sense primer SEQ ID NO:17 and antisense primer SEQ ID NO:23,
   (d) sense primer SEQ ID NO:18 and antisense primer SEQ ID NO:24,
   (e) sense primer SEQ ID NO:19 and antisense primer SEQ ID NO:23, and
   (f) sense primer SEQ ID NO:20 and antisense primer SEQ ID NO:24.

3. The endoglucanase of claim 2, wherein the PCR fragment amplified by using set (e) or (f) of oligonucleotides has a size of at least 159 base pairs.

4. The endoglucanase of claim 2, wherein the PCR fragment amplified by using set (c) or (d) of oligonucleotides has a size af at least 510 base pairs.

5. The endoglucanase of claim 2, wherein the PCR fragment amplified by using set (a) or (b) of oligonucleotides has a size af at least 288 base pairs.

6. The endoglucanase of claim 2 which is obtained from a strain belonging to a genus selected from the group consisting of Humicola, Trichoderma, Myceliophthora, Phanerochaete, Schizophyllum, Penicillium, Aspergillus, and Geotricum.

7. The endoglucanase of claim 2 which is obtained from a strain of Fusarium.

8. The endoglucanase of claim 7 which is obtained from *Fusarium oxysporum*.

9. The endoglucanase of claim 8 which is obtained from *Fusarium oxysporum* DSM 2672.

10. The endoglucanase of claim 9 which comprises amino acids 20–357 of SEQ ID NO:4.

11. A detergent additive comprising the endoglucanase of claim 2 in the form of a non-dusting granulate, stabilized liquid or protected enzyme.

12. The detergent additive of claim 11, further comprising one or more proteases having a higher degree of specificity than a *Bacillus lentus* serine protease.

13. The detergent additive of claim 12, wherein the one or more proteases are selected from the group consisting of subtilisin Novo or a variant thereof, a protease derived from *Nocardiopsis dassonvillei* NRRL 18133, a serine protease specific for glutamic and aspartic acid, derived from *Bacillus licheniformis,* and a trypsin-like protease derived from Fusarium sp. DSM 2672.

14. A detergent composition, comprising the endoglucanase of claim 2 and a surfactant.

15. A method of reducing the rate at which cellulose-containing fabrics become harsh or of reducing the harshness of cellulose-containing fabrics, comprising contacting the cellulose-containing fabrics with the endoglucanase of claim 2.

16. A method of providing color clarification of colored cellulose-containing fabrics, comprising contacting the colored cellulose-containing fabrics with the endoglucanase of claim 2.

17. A method of providing a localized variation in color of colored cellulose-containing fabrics, comprising treating the colored cotton-containing fabrics with the endoglucanase of claim 2.

18. A method of improving the drainage properties of paper pulp, comprising treating the paper pulp with the endoglucanase of claim 2.

19. An endoglucanase enzyme comprising the amino acids 1–284 of SEQ ID NO:2.

20. An endoglucanase comprising amino acids 20–357 of SEQ ID NO:4.

* * * * *

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
        (A) LENGTH: 1060 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Humicola insolens
        (B) STRAIN: DSM 1800

(ix) FEATURE:
        (A) NAME/KEY: mat_peptide
        (B) LOCATION: 73..924

(ix) FEATURE:
        (A) NAME/KEY: sig_peptide
        (B) LOCATION: 10..72

(ix) FEATURE:
        (A) NAME/KEY: CDS
        (B) LOCATION: 10..924

(xi) SEQUENCE DESCRIPTION: SEQ ID NO:1:

```
GGATCCAAG ATG CGT TCC TCC CCC CTC CTC CCG TCC GCC GTT GTG GCC         48
          Met Arg Ser Ser Pro Leu Leu Pro Ser Ala Val Val Ala
          -21 -20                 -15                 -10

GCC CTG CCG GTG TTG GCC CTT GCC GCT GAT GGC AGG TCC ACC CGC TAC       96
Ala Leu Pro Val Leu Ala Leu Ala Ala Asp Gly Arg Ser Thr Arg Tyr
            -5                   1                   5

TGG GAC TGC TGC AAG CCT TCG TGC GGC TGG GCC AAG AAG GCT CCC GTG      144
Trp Asp Cys Cys Lys Pro Ser Cys Gly Trp Ala Lys Lys Ala Pro Val
     10                  15                  20

AAC CAG CCT GTC TTT TCC TGC AAC GCC AAC TTC CAG CGT ATC ACG GAC      192
Asn Gln Pro Val Phe Ser Cys Asn Ala Asn Phe Gln Arg Ile Thr Asp
 25                  30                  35                  40

TTC GAC GCC AAG TCC GGC TGC GAG CCG GGC GGT GTC GCC TAC TCG TGC      240
Phe Asp Ala Lys Ser Gly Cys Glu Pro Gly Gly Val Ala Tyr Ser Cys
                 45                  50                  55

GCC GAC CAG ACC CCA TGG GCT GTG AAC GAC GAC TTC GCG CTC GGT TTT      288
Ala Asp Gln Thr Pro Trp Ala Val Asn Asp Asp Phe Ala Leu Gly Phe
             60                  65                  70

GCT GCC ACC TCT ATT GCC GGC AGC AAT GAG GCG GGC TGG TGC TGC GCC      336
Ala Ala Thr Ser Ile Ala Gly Ser Asn Glu Ala Gly Trp Cys Cys Ala
         75                  80                  85

TGC TAC GAG CTC ACC TTC ACA TCC GGT CCT GTT GCT GGC AAG AAG ATG      384
Cys Tyr Glu Leu Thr Phe Thr Ser Gly Pro Val Ala Gly Lys Lys Met
     90                  95                 100
```

| | | | | | | | | | | | | |
|---|---|---|---|---|---|---|---|---|---|---|---|---|
| GTC | GTC | CAG | TCC | ACC | AGC | ACT | GGC | GGT | GAT | CTT | GGC | AGC | AAC | CAC | TTC | 432 |
| Val | Val | Gln | Ser | Thr | Ser | Thr | Gly | Gly | Asp | Leu | Gly | Ser | Asn | His | Phe | |
| 105 | | | | | 110 | | | | | 115 | | | | | 120 | |

```
GTC GTC CAG TCC ACC AGC ACT GGC GGT GAT CTT GGC AGC AAC CAC TTC         432
Val Val Gln Ser Thr Ser Thr Gly Gly Asp Leu Gly Ser Asn His Phe
105                 110                 115                 120

GAT CTC AAC ATC CCC GGC GGC GGC GTC GGC ATC TTC GAC GGA TGC ACT         480
Asp Leu Asn Ile Pro Gly Gly Gly Val Gly Ile Phe Asp Gly Cys Thr
                125                 130                 135

CCC CAG TTC GGC GGT CTG CCC GGC CAG CGC TAC GGC GGC ATC TCG TCC         528
Pro Gln Phe Gly Gly Leu Pro Gly Gln Arg Tyr Gly Gly Ile Ser Ser
            140                 145                 150

CGC AAC GAG TGC GAT CGG TTC CCC GAC GCC CTC AAG CCC GGC TGC TAC         576
Arg Asn Glu Cys Asp Arg Phe Pro Asp Ala Leu Lys Pro Gly Cys Tyr
                155                 160                 165

TGG CGC TTC GAC TGG TTC AAG AAC GCC GAC AAT CCG AGC TTC AGC TTC         624
Trp Arg Phe Asp Trp Phe Lys Asn Ala Asp Asn Pro Ser Phe Ser Phe
170                 175                 180

CGT CAG GTC CAG TGC CCA GCC GAG CTC GTC GCT CGC ACC GGA TGC CGC         672
Arg Gln Val Gln Cys Pro Ala Glu Leu Val Ala Arg Thr Gly Cys Arg
185                 190                 195                 200

CGC AAC GAC GAC GGC AAC TTC CCT GCC GTC CAG ATC CCC TCC AGC AGC         720
Arg Asn Asp Asp Gly Asn Phe Pro Ala Val Gln Ile Pro Ser Ser Ser
                205                 210                 215

ACC AGC TCT CCG GTC AAC CAG CCT ACC AGC ACC AGC ACC ACG TCC ACC         768
Thr Ser Ser Pro Val Asn Gln Pro Thr Ser Thr Ser Thr Thr Ser Thr
            220                 225                 230

TCC ACC ACC TCG AGC CCG CCA GTC CAG CCT ACG ACT CCC AGC GGC TGC         816
Ser Thr Thr Ser Ser Pro Pro Val Gln Pro Thr Thr Pro Ser Gly Cys
        235                 240                 245

ACT GCT GAG AGG TGG GCT CAG TGC GGC GGC AAT GGC TGG AGC GGC TGC         864
Thr Ala Glu Arg Trp Ala Gln Cys Gly Gly Asn Gly Trp Ser Gly Cys
250                 255                 260

ACC ACC TGC GTC GCT GGC AGC ACT TGC ACG AAG ATT AAT GAC TGG TAC         912
Thr Thr Cys Val Ala Gly Ser Thr Cys Thr Lys Ile Asn Asp Trp Tyr
265                 270                 275                 280

CAT CAG TGC CTG TAGACGCAGG GCAGCTTGAG GGCCTTACTG GTGGCCGCAA             964
His Gln Cys Leu

CGAAATGACA CTCCCAATCA CTGTATTAGT TCTTGTACAT AATTTCGTCA TCCCTCCAGG       1024

GATTGTCACA TAAATGCAAT GAGGAACAAT GAGTAC                                 1060
```

(2) INFORMATION FOR SEQ ID NO:2:

(i) SEQUENCE CHARACTERISTICS:
        (A) LENGTH: 305 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Ser Ser Pro Leu Leu Pro Ser Ala Val Val Ala Ala Leu Pro
-21 -20                 -15                 -10

Val Leu Ala Leu Ala Ala Asp Gly Arg Ser Thr Arg Tyr Trp Asp Cys
-5                  1                   5                   10

Cys Lys Pro Ser Cys Gly Trp Ala Lys Lys Ala Pro Val Asn Gln Pro
                15                  20                  25

Val Phe Ser Cys Asn Ala Asn Phe Gln Arg Ile Thr Asp Phe Asp Ala
            30                  35                  40

Lys Ser Gly Cys Glu Pro Gly Gly Val Ala Tyr Ser Cys Ala Asp Gln
        45                  50                  55

Thr Pro Trp Ala Val Asn Asp Asp Phe Ala Leu Gly Phe Ala Ala Thr
60                  65                  70                  75
```

```
Ser Ile Ala Gly Ser Asn Glu Ala Gly Trp Cys Cys Ala Cys Tyr Glu
            80                  85                  90

Leu Thr Phe Thr Ser Gly Pro Val Ala Gly Lys Lys Met Val Val Gln
            95                  100                 105

Ser Thr Ser Thr Gly Gly Asp Leu Gly Ser Asn His Phe Asp Leu Asn
            110                 115                 120

Ile Pro Gly Gly Gly Val Gly Ile Phe Asp Gly Cys Thr Pro Gln Phe
            125                 130                 135

Gly Gly Leu Pro Gly Gln Arg Tyr Gly Gly Ile Ser Ser Arg Asn Glu
140                 145                 150                 155

Cys Asp Arg Phe Pro Asp Ala Leu Lys Pro Gly Cys Tyr Trp Arg Phe
            160                 165                 170

Asp Trp Phe Lys Asn Ala Asp Asn Pro Ser Phe Ser Phe Arg Gln Val
            175                 180                 185

Gln Cys Pro Ala Glu Leu Val Ala Arg Thr Gly Cys Arg Arg Asn Asp
            190                 195                 200

Asp Gly Asn Phe Pro Ala Val Gln Ile Pro Ser Ser Ser Thr Ser Ser
            205                 210                 215

Pro Val Asn Gln Pro Thr Ser Thr Ser Thr Thr Ser Thr Ser Thr Thr
220                 225                 230                 235

Ser Ser Pro Pro Val Gln Pro Thr Thr Pro Ser Gly Cys Thr Ala Glu
            240                 245                 250

Arg Trp Ala Gln Cys Gly Gly Asn Gly Trp Ser Gly Cys Thr Thr Cys
            255                 260                 265

Val Ala Gly Ser Thr Cys Thr Lys Ile Asn Asp Trp Tyr His Gln Cys
            270                 275                 280

Leu
```

(2) INFORMATION FOR SEQ ID NO:3:

(i) SEQUENCE CHARACTERISTICS:
        (A) LENGTH: 1473 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Fusarium oxysporum
        (B) STRAIN: DSM 2672

(ix) FEATURE:
        (A) NAME/KEY: CDS
        (B) LOCATION: 97..1224

(xi) SEQUENCE DESCRIPTION: SEQ ID NO:3:

```
GAATTCGCGG CCGCTCATTC ACTTCATTCA TTCTTTAGAA TTACATACAC TCTCTTTCAA        60

AACAGTCACT CTTTAAACAA AACAACTTTT GCAACA ATG CGA TCT TAC ACT CTT        114
                                       Met Arg Ser Tyr Thr Leu
                                         1               5

CTC GCC CTG GCC GGC CCT CTC GCC GTG AGT GCT GCT TCT GGA AGC GGT        162
Leu Ala Leu Ala Gly Pro Leu Ala Val Ser Ala Ala Ser Gly Ser Gly
            10                  15                  20

CAC TCT ACT CGA TAC TGG GAT TGC TGC AAG CCT TCT TGC TCT TGG AGC        210
His Ser Thr Arg Tyr Trp Asp Cys Cys Lys Pro Ser Cys Ser Trp Ser
        25                  30                  35
```

```
GGA AAG GCT GCT GTC AAC GCC CCT GCT TTA ACT TGT GAT AAG AAC GAC       258
Gly Lys Ala Ala Val Asn Ala Pro Ala Leu Thr Cys Asp Lys Asn Asp
     40              45                  50

AAC CCC ATT TCC AAC ACC AAT GCT GTC AAC GGT TGT GAG GGT GGT GGT       306
Asn Pro Ile Ser Asn Thr Asn Ala Val Asn Gly Cys Glu Gly Gly Gly
 55              60                  65                  70

TCT GCT TAT GCT TGC ACC AAC TAC TCT CCC TGG GCT GTC AAC GAT GAG       354
Ser Ala Tyr Ala Cys Thr Asn Tyr Ser Pro Trp Ala Val Asn Asp Glu
             75                  80                  85

CTT GCC TAC GGT TTC GCT GCT ACC AAG ATC TCC GGT GGC TCC GAG GCC       402
Leu Ala Tyr Gly Phe Ala Ala Thr Lys Ile Ser Gly Gly Ser Glu Ala
         90                  95                 100

AGC TGG TGC TGT GCT TGC TAT GCT TTG ACC TTC ACC ACT GGC CCC GTC       450
Ser Trp Cys Cys Ala Cys Tyr Ala Leu Thr Phe Thr Thr Gly Pro Val
     105                 110                 115

AAG GGC AAG AAG ATG ATC GTC CAG TCC ACC AAC ACT GGA GGT GAT CTC       498
Lys Gly Lys Lys Met Ile Val Gln Ser Thr Asn Thr Gly Gly Asp Leu
 120                 125                 130

GGC GAC AAC CAC TTC GAT CTC ATG ATG CCC GGT GGT GTC GGT ATC           546
Gly Asp Asn His Phe Asp Leu Met Met Pro Gly Gly Val Gly Ile
135                 140                 145                 150

TTC GAC GGC TGC ACC TCT GAG TTC GGC AAG GCT CTC GGC GGT GCC CAG       594
Phe Asp Gly Cys Thr Ser Glu Phe Gly Lys Ala Leu Gly Gly Ala Gln
             155                 160                 165

TAC GGC GGT ATC TCC TCC CGA AGC GAA TGT GAT AGC TAC CCC GAG CTT       642
Tyr Gly Gly Ile Ser Ser Arg Ser Glu Cys Asp Ser Tyr Pro Glu Leu
         170                 175                 180

CTC AAG GAC GGT TGC CAC TGG CGA TTC GAC TGG TTC GAG AAC GCC GAC       690
Leu Lys Asp Gly Cys His Trp Arg Phe Asp Trp Phe Glu Asn Ala Asp
     185                 190                 195

AAC CCT GAC TTC ACC TTT GAG CAG GTT CAG TGC CCC AAG GCT CTC CTC       738
Asn Pro Asp Phe Thr Phe Glu Gln Val Gln Cys Pro Lys Ala Leu Leu
 200                 205                 210

GAC ATC AGT GGA TGC AAG CGT GAT GAC GAC TCC AGC TTC CCT GCC TTC       786
Asp Ile Ser Gly Cys Lys Arg Asp Asp Asp Ser Ser Phe Pro Ala Phe
215                 220                 225                 230

AAG GTT GAT ACC TCG GCC AGC AAG CCC CAG CCC TCC AGC TCC GCT AAG       834
Lys Val Asp Thr Ser Ala Ser Lys Pro Gln Pro Ser Ser Ser Ala Lys
             235                 240                 245

AAG ACC ACC TCC GCT GCT GCT GCC GCT CAG CCC CAG AAG ACC AAG GAT       882
Lys Thr Thr Ser Ala Ala Ala Ala Gln Pro Gln Lys Thr Lys Asp
         250                 255                 260

TCC GCT CCT GTT GTC CAG AAG TCC TCC ACC AAG CCT GCC GCT CAG CCC       930
Ser Ala Pro Val Val Gln Lys Ser Ser Thr Lys Pro Ala Ala Gln Pro
     265                 270                 275

GAG CCT ACT AAG CCC GCC GAC AAG CCC CAG ACC GAC AAG CCT GTC GCC       978
Glu Pro Thr Lys Pro Ala Asp Lys Pro Gln Thr Asp Lys Pro Val Ala
 280                 285                 290

ACC AAG CCT GCT GCT ACC AAG CCC GTC CAA CCT GTC AAC AAG CCC AAG      1026
Thr Lys Pro Ala Ala Thr Lys Pro Val Gln Pro Val Asn Lys Pro Lys
295                 300                 305                 310

ACA ACC CAG AAG GTC CGT GGA ACC AAA ACC CGA GGA AGC TGC CCG GCC      1074
Thr Thr Gln Lys Val Arg Gly Thr Lys Thr Arg Gly Ser Cys Pro Ala
             315                 320                 325

AAG ACT GAC GCT ACC GCC AAG GCC TCC GTT GTC CCT GCT TAT TAC CAG      1122
Lys Thr Asp Ala Thr Ala Lys Ala Ser Val Val Pro Ala Tyr Tyr Gln
         330                 335                 340

TGT GGT GGT TCC AAG TCC GCT TAT CCC AAC GGC AAC CTC GCT TGC GCT      1170
Cys Gly Gly Ser Lys Ser Ala Tyr Pro Asn Gly Asn Leu Ala Cys Ala
     345                 350                 355
```

-continued

```
ACT GGA AGC AAG TGT GTC AAG CAG AAC GAG TAC TAC TCC CAG TGT GTC    1218
Thr Gly Ser Lys Cys Val Lys Gln Asn Glu Tyr Tyr Ser Gln Cys Val
            360                 365                 370

CCC AAC TAAATGGTAG ATCCATCGGT TGTGGAAGAG ACTATGCGTC TCAGAAGGGA    1274
Pro Asn
375

TCCTCTCATG AGCAGGCTTG TCATTGTATA GCATGGCATC CTGGACCAAG TGTTCGACCC  1334

TTGTTGTACA TAGTATATCT TCATTGTATA TATTTAGACA CATAGATAGC CTCTTGTCAG  1394

CGACAACTGG CTACAAAAGA CTTGGCAGGC TTGTTCAATA TTGACACAGT TTCCTCCATA  1454

AAAAAAAAAA AAAAAAAAA                                              1473
```

(2) INFORMATION FOR SEQ ID NO:4:

(i) SEQUENCE CHARACTERISTICS:
        (A) LENGTH: 376 amino acids
        (B) TYPE: amino acid
        (D) TOPOLOGY: linear (ii) MOLECULE TYPE: protein (xi) SEQUENCE DESCRIPTION: SEQ ID NO:4:

```
Met Arg Ser Tyr Thr Leu Leu Ala Leu Ala Gly Pro Leu Ala Val Ser
1               5                   10                  15

Ala Ala Ser Gly Ser Gly His Ser Thr Arg Tyr Trp Asp Cys Cys Lys
                20                  25                  30

Pro Ser Cys Ser Trp Ser Gly Lys Ala Ala Val Asn Ala Pro Ala Leu
            35                  40                  45

Thr Cys Asp Lys Asn Asp Asn Pro Ile Ser Asn Thr Asn Ala Val Asn
        50                  55                  60

Gly Cys Glu Gly Gly Gly Ser Ala Tyr Ala Cys Thr Asn Tyr Ser Pro
65                  70                  75                  80

Trp Ala Val Asn Asp Glu Leu Ala Tyr Gly Phe Ala Ala Thr Lys Ile
                85                  90                  95

Ser Gly Gly Ser Glu Ala Ser Trp Cys Cys Ala Cys Tyr Ala Leu Thr
                100                 105                 110

Phe Thr Thr Gly Pro Val Lys Gly Lys Lys Met Ile Val Gln Ser Thr
            115                 120                 125

Asn Thr Gly Gly Asp Leu Gly Asp Asn His Phe Asp Leu Met Met Pro
        130                 135                 140

Gly Gly Gly Val Gly Ile Phe Asp Gly Cys Thr Ser Glu Phe Gly Lys
145                 150                 155                 160

Ala Leu Gly Gly Ala Gln Tyr Gly Gly Ile Ser Ser Arg Ser Glu Cys
                165                 170                 175

Asp Ser Tyr Pro Glu Leu Leu Lys Asp Gly Cys His Trp Arg Phe Asp
            180                 185                 190

Trp Phe Glu Asn Ala Asp Asn Pro Asp Phe Thr Phe Glu Gln Val Gln
        195                 200                 205

Cys Pro Lys Ala Leu Leu Asp Ile Ser Gly Cys Lys Arg Asp Asp Asp
    210                 215                 220

Ser Ser Phe Pro Ala Phe Lys Val Asp Thr Ser Ala Ser Lys Pro Gln
225                 230                 235                 240

Pro Ser Ser Ser Ala Lys Lys Thr Thr Ser Ala Ala Ala Ala Gln
                245                 250                 255

Pro Gln Lys Thr Lys Asp Ser Ala Pro Val Val Gln Lys Ser Ser Thr
            260                 265                 270
```

```
Lys Pro Ala Ala Gln Pro Glu Pro Thr Lys Pro Ala Asp Lys Pro Gln
    275                 280                 285

Thr Asp Lys Pro Val Ala Thr Lys Pro Ala Ala Thr Lys Pro Val Gln
    290                 295                 300

Pro Val Asn Lys Pro Lys Thr Thr Gln Lys Val Arg Gly Thr Lys Thr
305                 310                 315                 320

Arg Gly Ser Cys Pro Ala Lys Thr Asp Ala Thr Ala Lys Ala Ser Val
                325                 330                 335

Val Pro Ala Tyr Tyr Gln Cys Gly Gly Ser Lys Ser Ala Tyr Pro Asn
                340                 345                 350

Gly Asn Leu Ala Cys Ala Thr Gly Ser Lys Cys Val Lys Gln Asn Glu
                355                 360                 365

Tyr Tyr Ser Gln Cys Val Pro Asn
370                 375
```

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

AGCTGCGGCC GCAGGCCGCG GAGGCCA                                    27

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

AGCTTGGCCT CCGCGGCCTG CGGCCGC                                    27

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AATTCGCGGC CGCGGCCATG GAGGCC                                     26

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

AATTGGCCTC CATGGCCGCG GCCGCG                                     26

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

AAYGCYGACA AAYCC                                          15

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

AACGAYGAYG GNAAYTTCCC                                   20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

AAYGAYTGGT ACCAYCARTG                                   20

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GCGCCAGTAG CAGCCGGGCT TGAGGG                           26

(2) INFORMATION FOR SEQ ID NO:13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

ACGTCTCAAC TCGGATCCAA GATGCGTT                       28

(2) INFORMATION FOR SEQ ID NO:14:

(i) SEQUENCE CHARACTERISTICS:

```
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

CTCAACTCTG ATCAAGATGC GTTCC                                              25

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

TGTCGACCAG TAAGGCCCTC AAGCTG                                             26

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:16:

GACAGAGCAC AGAATTCACT AGTGAGCTCT                                         30

(2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

TGGGAYTGYT GYAARCC                                                       17

(2) INFORMATION FOR SEQ ID NO:18:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

AGGGAGACCG GAATTCTGGG AYTGYTGYAA RCC                                     33

(2) INFORMATION FOR SEQ ID NO:19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO:19:

CCNGGNGGNG GNGTNGG                                                  17

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

AGGGAGACCG GAATTCCCNG GNGGNGGNGT NGG                                 33

(2) INFORMATION FOR SEQ ID NO:21:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

ACNAYCATNK TYTTNCC                                                  17

(2) INFORMATION FOR SEQ ID NO:22:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

GACAGAGCAC AGAATTCACN AYCATNKTYT TNCC                                34

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

NGGRTTRTCN GCNKYYTYRA ACCA                                          24

(2) INFORMATION FOR SEQ ID NO:24:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

GACAGAGCAC AGAATTCNGG RTTRTCNGCN KYYTYRAACC A                        41

(2) INFORMATION FOR SEQ ID NO:25:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

```
GGGGTAGCTA TCACATTCGC TTCGGGAGGA GATACCGCCG TA                          42
```

(2) INFORMATION FOR SEQ ID NO:26:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

```
CTTCTTGCTC TTGGAGCGGA AAGGCTGCTG TCAACGCCCC TG                          42
```

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

```
TGTACGCATG TAACATTA                                                     18
```

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

```
CTGCACAATA TTTCAAGC                                                     18
```

(2) INFORMATION FOR SEQ ID NO:29:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

```
GGGGTAGCTA TCACATTCGC TTCGGGAGGA GATACCGCCG TA                          42
```

(2) INFORMATION FOR SEQ ID NO:30:

(i) SEQUENCE CHARACTERISTICS:

```
            (A) LENGTH: 42 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:30:

CTTCTTGCTC TTGGAGCGGA AAGGCTGCTG TCAACGCCCC TG                           42

(2) INFORMATION FOR SEQ ID NO:31:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:31:

AGCTTCTCAA GGACGGTT                                                      18

(2) INFORMATION FOR SEQ ID NO:32:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:32:

AACAAGGGTC GAACACTT                                                      18

(2) INFORMATION FOR SEQ ID NO:33:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:33:

CCAGAAGACC AAGGATT                                                       17
```